(12) United States Patent
Parab et al.

(10) Patent No.: US 11,728,028 B2
(45) Date of Patent: Aug. 15, 2023

(54) CLINICAL SERVICES PATIENT MANAGEMENT SYSTEM

(71) Applicant: Rite Aid, Camp Hill, PA (US)

(72) Inventors: Rageshree V. Parab, Mechanicsburg, PA (US); Lynne M. Shirk, Lewisberry, PA (US)

(73) Assignee: Rite Aid Hdqtrs. Corp., Etters, PA (US)

( * ) Notice: Subject to any disclaimer, the term of this patent is extended or adjusted under 35 U.S.C. 154(b) by 740 days.

(21) Appl. No.: 16/775,911

(22) Filed: Jan. 29, 2020

(65) Prior Publication Data

US 2021/0233650 A1    Jul. 29, 2021

(51) Int. Cl.
| | | |
|---|---|---|
| *G16H 40/20* | (2018.01) | |
| *G06Q 30/0601* | (2023.01) | |
| *G06F 16/958* | (2019.01) | |
| *G06F 16/9535* | (2019.01) | |
| *G16H 20/10* | (2018.01) | |

(Continued)

(52) U.S. Cl.
CPC .......... *G16H 40/20* (2018.01); *G06F 3/0482* (2013.01); *G06F 16/958* (2019.01); *G06F 16/9535* (2019.01); *G06Q 10/10* (2013.01); *G06Q 20/202* (2013.01); *G06Q 30/0627* (2013.01); *G16H 10/60* (2018.01); *G16H 20/10* (2018.01); *G16H 40/67* (2018.01)

(58) Field of Classification Search
CPC ........ G16H 40/20; G16H 10/60; G16H 20/10; G16H 40/67; G06F 3/0482; G06F 16/9535; G06F 16/958; G06Q 10/10; G06Q 20/202; G06Q 30/0627; G06Q 20/102; G06Q 20/145; G07F 17/0092
USPC ........................................................ 705/2–3
See application file for complete search history.

(56) References Cited

U.S. PATENT DOCUMENTS

| | | | |
|---|---|---|---|
| 2006/0247973 A1* | 11/2006 | Mueller .................. | G06Q 20/20 705/26.1 |
| 2008/0015939 A1* | 1/2008 | Walker ............... | G06Q 30/0207 705/14.1 |

(Continued)

FOREIGN PATENT DOCUMENTS

WO    WO-2006036712 A2 *    4/2006    ......... G06F 19/3456

*Primary Examiner* — Joy Chng
(74) *Attorney, Agent, or Firm* — Culhane Meadows PLLC; Michael P. Dunnam

(57) ABSTRACT

A pharmacy analytics system generates clinical opportunities for patients, and the resulting opportunity file is sent to the pharmacy management system mainframe for distribution to pharmacy management systems in respective pharmacies. The clinical programs and opportunities configured in the system include immunizations, Medication Therapy Management, performance measurement, predictive refills, and the like. Opportunities for a particular patient will only be synchronized to the stores that are subscribed to by the particular patient. All clinical opportunities are sent down by the pharmacy management system mainframe to a pharmacy management system client as part of a data synchronization process or in response to a customer browse and customer select transactions. The clinical opportunities are then presented during interactions with the customer in the prescription workflow when filling prescriptions using the pharmacy management system and/or in response to a search.

30 Claims, 12 Drawing Sheets

(51) Int. Cl.
*G06Q 10/10* (2023.01)
*G06Q 20/20* (2012.01)
*G06F 3/0482* (2013.01)
*G16H 10/60* (2018.01)
*G16H 40/67* (2018.01)

(56) References Cited

U.S. PATENT DOCUMENTS

| | | | | |
|---|---|---|---|---|
| 2009/0138365 | A1* | 5/2009 | Mueller | G06Q 30/0217 705/16 |
| 2012/0290349 | A1* | 11/2012 | Burkhart | G06Q 30/06 705/7.13 |
| 2014/0278495 | A1* | 9/2014 | Rourke | G06Q 10/06315 705/2 |
| 2015/0100442 | A1* | 4/2015 | Van Heerden | G06Q 20/327 705/16 |

* cited by examiner

CLINICAL SERVICES PATIENT MANAGEMENT SYSTEM

TECHNICAL FIELD

This application is related to systems and methods for notifying users of opportunities for clinical services and, more particularly, to methods for gathering analytical data relating to clinical services provided to patients by pharmacists and identifying opportunities for clinical services.

BACKGROUND

Existing pharmacy management systems generally do not provide any functionality for notifying users of opportunities for clinical services. Instead, technicians and/or pharmacists must manually identify potential opportunities by examining patient profiles. Additionally, there is no method for gathering analytical data relating to pharmacists providing patients with a service as a result of identifying such opportunities.

Pharmacy analytics systems such as a data warehouse system provided by 1010Data enable pharmacies to leverage their pharmacy data to enable insights-based decision-making. Such systems enable pharmacies to better understand how customers shop in the stores and to drive sales growth by leveraging the collected data. However, such systems do not enable the stores to track the patients' prescription data and to recommend clinical services based on such data. It is desirable to leverage such systems to identify clinical opportunities such as immunizations, medication therapy management (MTM), etc. at a patient level.

SUMMARY

Various details for the embodiments of the inventive subject matter are provided in the accompanying drawings and in the detailed description text below.

The systems and methods described herein provide a technique that leverages data from pharmacy analytics systems to identify clinical opportunities such as immunizations, MTM, etc. at a patient level. The compiled data is used by the pharmacy management system to present users of the pharmacy management system with the opportunities via a new screen incorporated into the prescription workflow.

Queries are created in the pharmacy analytics system that generate clinical opportunities for patients, and the resulting opportunity file is sent to a pharmacy management system mainframe for distribution to the respective stores. In sample embodiments, the clinical opportunities are imported into the pharmacy management system mainframe for a plurality of pharmacy management systems, and the pharmacy management system mainframe uses customer subscription tables to synchronize the opportunity files down to the respective stores. In the sample embodiments, the clinical programs and opportunities configured in the system include immunizations, MTM, performance measurement, predictive refills, and the like. Opportunities for a particular patient will only be synchronized to the stores that are subscribed to by the particular patient. All clinical opportunities are sent down by the pharmacy management system mainframe to a pharmacy management system client for customers as part of the mainframe-client synchronization process. The clinical opportunities also get pulled down by the client when a central search is performed by the client through customer select and customer browse transactions. The clinical opportunities are then presented during interactions with the customer when filling prescriptions using the pharmacy management system and/or when concluding a prescription sale at a Point of Sale (POS) system in the store.

In sample embodiments, a method of providing clinical services is provided that includes analyzing pharmacy data to generate clinical opportunities for patients; providing files containing the clinical opportunities to a central pharmacy management system; the central pharmacy management system distributing clinical opportunities to pharmacy management systems in respective pharmacies based on customers registered with each respective pharmacy; and presenting clinical opportunities for a customer during interactions with the customer in a prescription workflow when filling prescriptions using a pharmacy management system or when concluding a sale for a prescription at a Point of Sale (POS) system in a pharmacy at which the customer is registered. In the sample embodiments, the clinical opportunities may include an immunization, medication therapy management, performance measurement, a predictive refill, and the like.

In the sample embodiments, a configuration portal may be provided that is accessible by corporate users and editable only by business partners. The data configured using the configuration portal is saved in a central database on the mainframe and is synchronized to the client. The configuration portal enables a user to add and to configure clinical opportunities and actions associated with the generated clinical opportunities. The configuration portal also enables the user to search for clinical programs including clinical opportunities based on a program description for the clinical programs and a designated user level. The configuration portal further enables the user to add a new clinical program and a user level and to specify a suppression type for a clinical program. In sample embodiments, the suppression type for a clinical program suppresses opportunities for the customer during the prescription workflow. The configuration portal further enables the user to edit at least a program description, a user level, and the suppression type for a clinical program from a clinical program search screen. The configuration portal may also enable the user to create a clinical opportunity and to assign and unassign web links to a clinical opportunity. The configuration portal may also enable the user to add and to edit clinical opportunities and to display an action associated with one or more clinical programs.

In further sample embodiments, the central pharmacy management system processes the files containing the clinical opportunities in response to user queries to identify clinical opportunities at one or more pharmacies at which the customer is registered. The central pharmacy management system also periodically synchronizes new data from the processed files, actions taken by the pharmacy management system when responding to a clinical opportunity, and configuration data among the central pharmacy management system, the pharmacy management system, and the POS system. The actions to be taken in response to respective clinical opportunities are also synchronized between the central pharmacy management system and the one or more pharmacies at which the customer is registered. Also, when a patient has indicated interest in the opportunity, an action has been taken to address the opportunity, and the pharmacist has reviewed the action taken, the clinical opportunity is de-identified in a list of available opportunities.

In still further sample embodiments, a clinical opportunities screen is inserted into the prescription workflow when filling prescriptions using the pharmacy management system and a search interface is provided that enables a user to search for available clinical opportunities and to launch a selected clinical opportunity to perform identified activities. A clinical opportunities screen also may be inserted into a checkout at a Point of Sale (POS) system that presents available opportunities for a patient during a checkout process. The clinical opportunities for a customer may be presented to a clinical opportunities screen on a display. The clinical opportunities screen may be configurable based on priorities of the clinical opportunities.

In other sample embodiments, a "Patient not interested" button is added to a clinical opportunity on the clinical opportunities screen when a patient has indicated no interest in the clinical opportunity. The clinical opportunities screen may also present a button that, upon selection, allows a user to access a clinical opportunity search screen that produces search results from which a clinical opportunity may be launched. Also, the clinical opportunities screen may be automatically launched after a user has selected a medication using the pharmacy management system or when the user opens a prescription in a product review status. A dedicated button on a medication history screen of the pharmacy management system may also be provided that launches a clinical opportunities screen for the patient upon selection. A dedicated button may also be added on an order summary screen of the pharmacy management system that launches a clinical opportunities screen for the patient upon selection.

In still other sample embodiments, a clinical opportunity is suppressed during the prescription workflow when a prescription being dispensed addresses the clinical opportunity. Available clinical opportunities are presented to a user of the pharmacy management system when the pharmacy management system is in a product review status irrespective of whether or not the clinical opportunity already has been addressed. A clinical opportunity at a second pharmacy where the customer is registered may also be suppressed when the clinical opportunity has been acted upon in a first pharmacy at which the customer is registered.

In still further sample embodiments, a list of clinical opportunities shown to a user of the pharmacy management system in the prescription workflow is captured and a report including the list of clinical opportunities is prepared. Also, clinical opportunities are removed from the central pharmacy management system as the clinical opportunities reach their expiration dates. A record of actions taken with respect to clinical opportunities may also be maintained.

In accordance with other aspects, the methods described herein are implemented by a clinical services system comprising an opportunity system that analyzes pharmacy data to generate clinical opportunities for patients and generates files containing the clinical opportunities, a central pharmacy management system that receives the files containing the clinical opportunities and distributes clinical opportunities to pharmacy management systems in respective pharmacies based on customers registered with each respective pharmacy, and a pharmacy management system in a pharmacy at which a customer is registered. The pharmacy management system implements a prescription workflow to fill prescriptions and presents clinical opportunities for the customer during interactions with the customer in the prescription workflow. A Point of Sale (POS) system in the pharmacy at which the customer is registered may also present clinical opportunities for the customer when concluding a sale for a prescription.

As discussed herein, the logic, commands, or instructions that implement aspects of the methods described herein may be provided in a computing system including any number of form factors for the computing system such as desktop or notebook personal computers, mobile devices such as tablets, netbooks, and smartphones, client terminals and server-hosted machine instances, and the like. Another embodiment discussed herein includes the incorporation of the techniques discussed herein into other forms, including into other forms of programmed logic, hardware configurations, or specialized components or modules, including an apparatus with respective means to perform the functions of such techniques. The respective algorithms used to implement the functions of such techniques may include a sequence of some or all of the electronic operations described herein, or other aspects depicted in the accompanying drawings and detailed description below. Such systems and computer-readable media including instructions for implementing the methods described herein also constitute sample embodiments.

This summary section is provided to introduce aspects of the inventive subject matter in a simplified form, with further explanation of the inventive subject matter following in the text of the detailed description. This summary section is not intended to identify essential or required features of the claimed subject matter, and the particular combination and order of elements listed this summary section is not intended to provide limitation to the elements of the claimed subject matter. Rather, it will be understood that the following section provides summarized examples of some of the embodiments described in the Detailed Description below.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments discussed in the present document.

DETAILED DESCRIPTION

Figure 1:
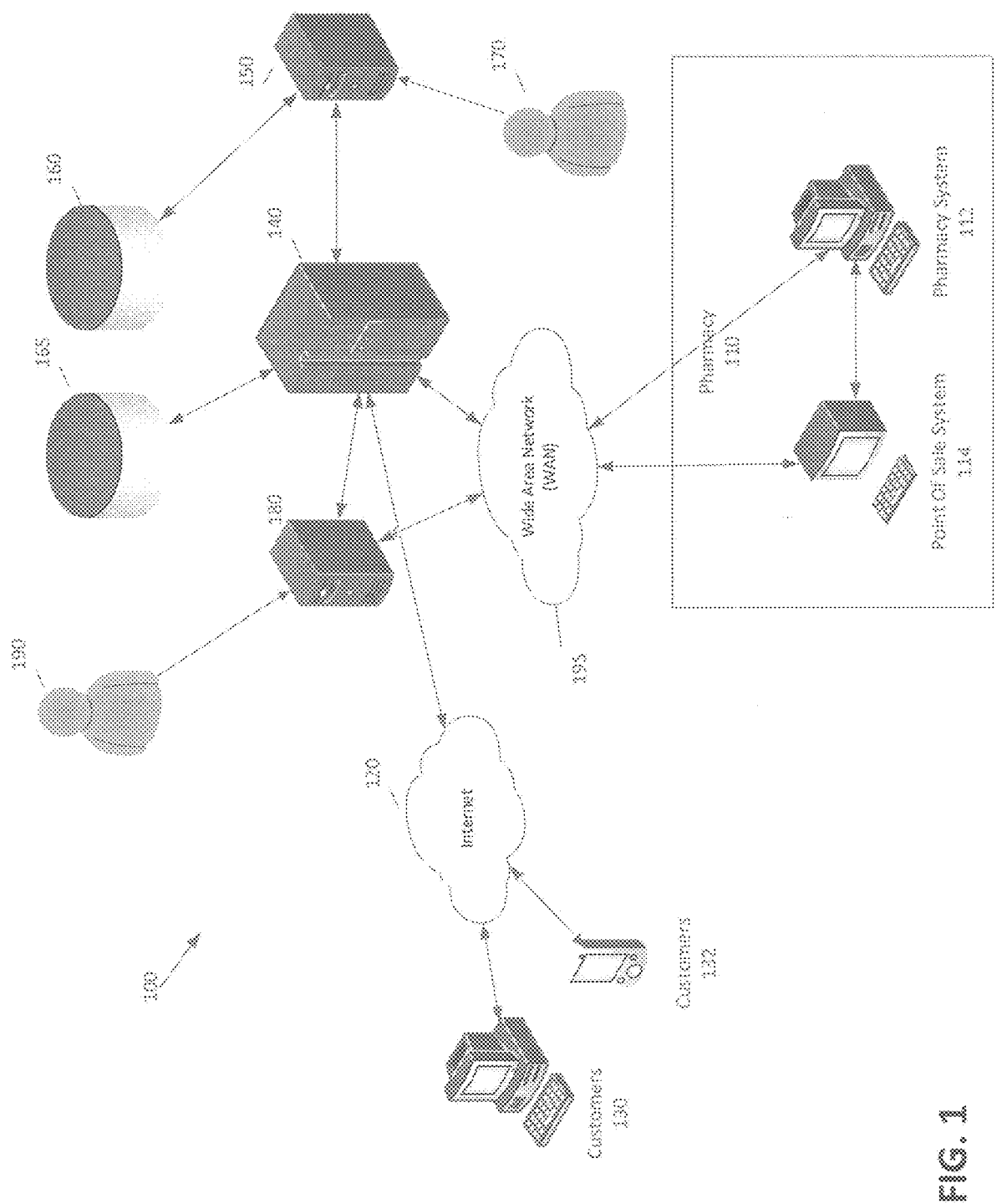
FIG. 1 illustrates an overview of a clinical services patient management system in a sample embodiment.

The following description with respect to FIGS. 1-10 sufficiently illustrates specific embodiments to enable those skilled in the art to practice them. Other embodiments may incorporate structural, logical, process, and other changes. Portions and features of some embodiments may be included in, or substituted for, those of other embodiments. Embodiments set forth in the claims encompass all available equivalents of those claims. The example embodiments are presented for illustrative purposes only and are not intended to be restrictive or limiting on the scope of the disclosure or the claims presented herein.

The functions described herein may be implemented in software in one embodiment. The software may consist of computer executable instructions stored on computer readable media or computer readable storage device such as one or more non-transitory memories or other type of hardware-based storage devices, either local or networked. Further, such functions correspond to modules, which may be software, hardware, firmware, or any combination thereof. Multiple functions may be performed in one or more modules as desired, and the embodiments described are merely examples. The software may be executed on a digital signal processor, ASIC, microprocessor, or other type of processor operating on a computer system, such as a personal computer, server, or other computer system, turning such computer system into a specifically programmed machine.

Terms and Definitions

Automated Courtesy Refill (ACR): ACR is an opportunity under the program 'Predictive Refill.'

Data Warehouse: A large store of data accumulated from a wide range of sources within a company and used to guide management decisions.

GCSN: Generic Code Sequence Number is a unique number that groups drugs into categories such as active ingredients, strength, route of administration, and dosage.

ILE: The initial load extract process is performed when opening a new store or performing a store start-over in the event of complete hardware failure. The ILE is responsible for pulling data from the mainframe to populate local database tables. For example, the ILE process may need to be updated to pull static data such as program and opportunity definitions, configurations, etc. as well as the patient level opportunities and associated action data.

MTM: Medication Therapy Management is a service provided by a pharmacist to their patients which assists in ensuring proper therapeutic treatment and aims to increase overall medication adherence by patients and address gaps in therapy.

NexGen: A Pharmacy Management Application implemented by Rite Aid Corporation as a prescription order fulfillment and customer notification system.

Opportunity: An opportunity is a system defined set of circumstances for providing various clinical services that a patient has met. For example, the opportunity may address a gap in the patient's medical care. Sample opportunities include a Pneumovax 23 (65+) vaccine, a Statin-Red Star-Adherence consultation, a prescription refill, and the like.

Opportunity System: A data warehouse analytics solution provided by pharmacy analytics vendors.

OTR: One Trip Refills is a refill program that allows enrolled patients to have all of their prescriptions picked up on the same date.

Portal: A website that provides access to a wide array of web based applications for both store and/or corporate users.

Program: A program is a high-level area of focus for which to identify and present patient opportunities. Examples of a program include, but are not limited to, immunization, MTM, predictive refill and performance measurement.

SQL: Structured Query Language is a database query language used to obtain and/or manipulate data in a database.

Process Overview

Queries are created in the pharmacy analytics system that generate clinical opportunities for patients, and the resulting opportunity files are sent to the pharmacy management system mainframe for distribution to the pharmacy management systems in respective stores. In sample embodiments, the clinical opportunities are imported into a pharmacy management system mainframe, and the pharmacy management system mainframe uses customer subscription tables to synchronize the opportunity files down to the respective stores using a data synchronization process. In the sample embodiments, the clinical programs and opportunities configured in the system include immunizations (e.g., flu shots), MTM (e.g., Outcomes, performance measurement (e.g., Red Star Adherence Consultation), predictive refills (e.g., One Trip Refills (OTR) and Automated Courtesy Refills (ACR)), and the like. Opportunities for a particular patient will only be synchronized to the stores that are subscribed to by the particular patient. All clinical opportunities are sent down by the pharmacy management system mainframe to a pharmacy management system client for customers as part of a mainframe-client synchronization process. The opportunities may also get pulled down when a central search is performed by the client through the customer select and customer browse transactions. The clinical opportunities are then presented during interactions with the customer in the prescription workflow when filling prescriptions using the pharmacy management system and/or when concluding a sale at a Point of Sale (POS) system in the store.

System Overview

FIG. 1 illustrates an overview of a clinical services patient management system 100 in a sample embodiment. As illustrated, the store housing the pharmacy 110 includes a pharmacy management system 112 that the pharmacist uses to fill prescriptions. The pharmacy 110 also includes a point of sale (POS) system 114 including one or more point of sale registers that may be used to complete the sale when the customer arrives to pick up a prescription. In sample embodiments, customers may interact with the pharmacy system 112 via the Internet 120 using one or more customer devices 130, 132 to electronically submit prescriptions to be filled and to receive notifications when the prescriptions are ready.

In sample embodiments, the clinical services patient management system 100 includes a pharmacy management system mainframe (or central) computer 140 that interacts with a pharmacy data analytics/opportunity system 150 that generates clinical opportunities as described herein. The pharmacy data is stored in a data warehouse/database 160 (e.g., SQL database) along with relevant store, customer, and prescription information. The mainframe computer 140 also includes a database 165 that stores data for the respective pharmacies, as described below. The user 170 may interact with the pharmacy data analytics/opportunity system 150 to submit queries to the pharmacy data stored in the data warehouse to 160 identify the opportunities described herein. A portal system 180 also enables the user 190 to add and to configure programs and opportunities for implementation by the pharmacy data analytics/opportunity system 150 to generate the opportunities described herein and to add/modify the actions associated with the generated opportunities.

In sample embodiments, the pharmacy management system 112 implements the NexGen Pharmacy Management Application implemented by Rite Aid Corporation as a prescription order fulfillment and customer notification system. The pharmacy management system 112 provides a dispensing flow to the pharmacist. Also, as described below, the pharmacy management system 112 is modified to enable the pharmacist and/or technician to search for and respond to clinical opportunities for patients. As also described below, the POS system 114 may also provide the salesclerk with access to the clinical opportunities via an interface of the POS system 114 and to print point of care (POC) paperwork as needed.

In sample embodiments, the pharmacy data analytics/opportunity system 150 is a data warehouse system provided by 1010Data that evaluates pharmacy data in data warehouse/database 160 to identify opportunities and to report the same to the user 170 in response to a search and to the mainframe 140 for distribution to the respective pharmacies 110. The mainframe 140 processes the data received from the pharmacy data analytics/opportunity system 150 and sends responses to the pharmacy data analytics/opportunity system 150 in response to queries as appropriate. Also, the mainframe 140 synchronizes new data, actions taken by the pharmacy management system 112, and configuration data between the mainframe and the respective pharmacy management systems 112 and POS system 114 in different pharmacies 110. The pharmacy data is retained in tables in the database 165 and provided to the respective pharmacy management systems 112 and POS systems 114 at selected stores through the data synchronization process via the Wide Area Network 195. In this fashion, the mainframe 140 manages the implementation of opportunities identified by the clinical services patient management system 100.

During operation, the clinical services management system 100 identifies clinical opportunities for patients/customers by analyzing/querying the pharmacy data stored in database 160 using the pharmacy data analytics/opportunity system 150. The pharmacy data is stored in the mainframe database 165 and the data required for analytics is pushed from the mainframe database 165 to the data warehouse 160. The identified new opportunities are provided to the database 165 of the mainframe 140 periodically (e.g., daily) using, for example, File Transfer Protocol (FTP), and then provided to the pharmacy management systems 112 and POS system 114 of respective pharmacies 110 during periodic (e.g., every thirty minutes to one hour, with most of the data processing completed before the store opens) synchronization processes between the mainframe 140 and the pharmacy management systems 112 and POS system 114 of the respective pharmacies 110. As appropriate, customer inputs for opportunities are fed into the pharmacy management systems 112 by technicians or pharmacists. The actions taken in response to the identified opportunities are also synchronized to the corresponding pharmacies 110 for each customer. The opportunities are marked as pending until completed. Completed opportunities are also sent back to the mainframe 140 and to the pharmacy data analytics/opportunity system 150 to indicate that an opportunity has been completed.

Opportunity System 150

The pharmacy data analytics/opportunity system 150 receives and identifies clinical opportunities for patients based on available clinical programs. In sample embodiments, a large scale code based data management system for data warehousing such as a data warehouse system provided by 1010Data may be used as the data warehouse 160 and the associated pharmacy data analytics system 150 may implement the opportunity system described herein. The 1010Data system populates queries written to generate opportunities. Such a system enables users to submit queries to their pharmacy data stored in the data warehouse 160 to identify the clinical opportunities described herein. In such as system, the pharmacy data analytics/opportunity system 150 may execute queries regularly to target customers/patients for clinical opportunities. The opportunity system 150 may perform a full refresh of the configuration elements daily. In response to the queries, the data warehouse 160 creates a feed to the pharmacy management system mainframe 140 with opportunities for the registered customers at the respective pharmacies. The opportunities may be separated by store and include the following data elements:

Opportunity ID
Customer number
Date (optional)

All actions taken in response to opportunities from the pharmacy management system 112 are processed and fed back to the pharmacy data analytics/opportunity system. The pharmacy data analytics/opportunity system 150 appends all opportunity and action activity from the pharmacy management systems 112. Only the latest status for the opportunity and action from the pharmacy management systems 112 need to be stored. The responses from the pharmacy management systems 112 are processed before the queries can run to identify new opportunities. Once the opportunity is closed, the record will remain in the opportunity system 150 for future reference or reporting but is not sent again to the customer. Multiple versions of the same opportunity and customer could exist and are differentiated by the creation date of the opportunity. Outcomes data may be incorporated into the opportunity system 150 at the pharmacy management system mainframe 140. Customer merges may generate opportunities for the new customer record. For example, claims data from an external vendor may provide MTM opportunities.

The processing of data by the opportunity system 150 to update the pharmacy management system mainframe 140 follows a number of rules. For example, there is a configuration value that controls how many records are processed during the pharmacy management system mainframe 140 processing of opportunity system 150 records for each daily run. Regardless of the opportunity status on the pharmacy management system mainframe 140, if an opportunity sent from the opportunity system 150 search already exists on the pharmacy management system mainframe 140, then that record is not replaced. If an opportunity sent from the opportunity system 150 search does not already exist on the pharmacy management system mainframe 140, then the opportunity is inserted with a New (N) status with the creation date as the current date. If a Pending opportunity is omitted from the opportunity system 150, a soft delete is performed by marking the record as Deleted (D) for the opportunity system 150 to pick up that night. If a Deleted opportunity is omitted again, a physical delete is performed. If a New opportunity is omitted from the opportunity system 150, a soft delete is performed by marking the record as Removed (R) for the opportunity system 150 to pick up that night. If a Removed opportunity is omitted again, a physical delete from memory is performed. If a Closed (C) opportunity is omitted from the opportunity system 150, a physical delete from memory is performed.

The data used for generating the global patient opportunity list resides in the opportunity system data warehouse 160. Once compiled, the opportunities from the opportunity system 150 are sent to the database 165 of the pharmacy management system mainframe 140 and then synchronized to the servers of the respective stores' pharmacy management system 112 for all patients subscribed to a store. The pharmacy management system mainframe 140 provides selected opportunities for customers at the respective stores to which the customers are registered. New opportunities are compared to the opportunities stored in the pharmacy management system mainframe 140 and the storage tables for the opportunities are updated as appropriate. Similarly, the tables identifying the registered customers and the pharmacies that are part of the system are updated as appropriate based on update configuration data provided by the portal system 180. This updated data is then pushed to the respective pharmacies 110 during the synchronization process.

Customer Devices

The clinical services patient management system 100 described herein may be adapted to work with the customer's communication devices 130, 132 such as smart phones, laptops, personal computers, and the like without requiring the customer to download specific software or to have an account with the pharmacy. The customer's communication devices 130, 132 may be used to collect customer information, to authenticate the customer, to collect payment information, to authorize prescription pickup or delivery, etc. All that is required is Internet access to a web interface provided by the clinical services patient management system 100.

Pharmacy Management System 112

The pharmacy management system 112 functions in the conventional fashion. A pharmacy management system 112 such as the NexGen Pharmacy Management Application implemented by Rite Aid Corporation provides a system for prescription order fulfillment and customer notification. The pharmacy management system 112 provides a dispensing flow to the pharmacist. In a sample configuration, the dispensing flow includes:

1. Searching and selecting a patient for dispensing a prescription.
2. Scanning a prescription image for non-electronic or written prescriptions.
3. Searching and selecting a prescriber for dispensing the prescription.
4. Search and selecting the medication for dispensing the prescription.
5. Entering dispensing details.
6. Selecting a payment method and adjudication, which may include editing the customer's insurance data.
7. Reviewing the prescription data.
8. Performing drug utilization review.
9. Performing final product review.

Upon completion of the final product review, the prescription goes to Will Call. In sample embodiments described herein, a Clinical Opportunities screen is inserted into the prescription workflow to present available opportunities for a patient to the pharmacist during the process of filling the prescription. The Clinical Opportunities screen generally makes the pharmacist aware of the programs and clinical opportunities for which the patient may qualify. A search interface enables the pharmacist/technician to search the available opportunities and to launch a selected opportunity to perform the identified activities (e.g. administer a vaccine).

Point of Sale System 114

The point of sale (POS) system 114 completes the sale of the prescription to the customer. In sample embodiments, applications of the point of sale system 114 interface with the pharmacy system 112. For example, the point of sale system 114 supports the GetRxInfo service. GetRxInfo is a webservice called by a POS application of the POS system 114 when a prescription is scanned at the POS system 114 during a sale. The GetRxInfo service returns the data needed by the POS application of the POS system 114 to sell the prescription. Examples of the data needed by the POS application of the POS system 114 include the customer's date of birth, whether the customer's ID needs to be collected before the script can be sold, etc. The POS application of the POS system 114 calls the GetRxInfo webservice by passing the location, prescription (Rx) number, and date of service for the script that is to be sold. The query parameters are passed to the GetRxInfo service in a query string of the URL.

The response from the GetRxInfo service will be either a success message along with the data needed to sell the prescription or an error message if the prescription is not in a state to be sold. A successful response will be sent back to the client if the prescription is in will call status and POS data is available in the pharmacy management system 112. However, an error response may be sent back in following cases: the prescription is not found in the pharmacy management system 112, the prescription is found in the pharmacy management system 112 but is not in will call status, or the prescription is in will call status but POS data is not available in the pharmacy management system 112. The error response may include any or all of the following data elements: version number for the service, prescription location, prescription number, date of service, pharmacy system order number for the prescription, pharmacy system order item number for the prescription, response status, and error message. If the message is a success message, the success message may further include the pharmacy system customer number, customer name and birth date, customer pay amount for the prescription, whether tax has to be collected from the customer for the prescription and, if so, the amount of the tax. The success message also may identify if the payment is by cash, by commercial insurance plan, or by government backed insurance plan. If by insurance plan, the success message may also identify the insurance agency, plan and group.

The success message may also contain certain POS flags including, for example, the drug being dispensed and a prompt for a customer HIPAA acknowledgement message and customer authorization request for customer enrollment in certain programs at the POS system 114. The flags may also identify if the customer is in a certain program such as a senior program or a prescription refill program.

In sample embodiments, the POS system 114 displays certain prescription-level (e.g., prescription in progress/Will Call) and patient-level (e.g., Check Photo ID) notifications when prescriptions are scanned at the POS register 114. The notification text and display order of the different notifications are typically hard-coded into the application. Clicking/touching the notification text opens a detailed view containing multiple grids titled "Will Call/Work in Progress", "Consultations", "AOB Documents", and "Additional Information".

To implement the functionality described herein, a new notification is added that informs users that the patient for a scanned prescription qualifies for clinical opportunities as described herein. Upon clicking/touching the notification text, the detailed view should contain only two grids: "Script Notifications" and "Patient Notifications". The "Patient Notifications" grid should contain all patient-level notifications. Also, the notification text allows users to respond with a "Patient not interested" action for any clinical opportunities that are displayed and in closed status.

Notifications of clinical opportunities are displayed when the patient has any clinical opportunity present (regardless of opportunity status) where the action "Patient unavailable" has previously been selected by a user (technician or pharmacist) of the pharmacy management system 112, or the patient has a clinical opportunity present that is configured to be displayed in the POS system 114. When an opportunity has this configuration set, the opportunity notification will be displayed regardless of any actions taken, even if the opportunity is closed. The priority of the notification on the display is configurable. For each clinical opportunity that is displayed, if the program in which the opportunity belongs to is configured to have the "Patient not interested" action and the opportunity is in a Closed status, then the user will have the option to choose "Patient not interested" from the POS system 114. This will result in the same action being recorded as when "Patient not interested" is chosen from within the pharmacy management system 112.

In sample embodiments, when the user clicks on the "Patient not interested" button, the button will remain disabled while processing. If the "Patient not interested" action is successfully added to the opportunity, the button will remain disabled with the text "[DONE]" appended to it. If the "Patient not interested" action is not successfully added, then the button will become re-enabled.

A new configuration value may be available at the opportunity-level which, when set, will cause the POS system 114 to display a notification whenever the configured opportunity is present for a patient of a scanned prescription at the POS system 114. This notification will be displayed regardless of any action taken on the opportunity or lack thereof, even if the opportunity is closed.

Also, while the pharmacy management system 112 may provide many different actions for a technician/pharmacist to choose from when responding to an opportunity, the POS system 114 may only provide a "Patient not interested" option. If the patient is interested and a physical action is taken in the pharmacy management system 112, such as creating a prescription, enrolling in a refill service, etc., then the opportunity for the patient is de-identified in the next daily feed of available opportunities by the opportunity system 150. Under normal requirements of the pharmacy management system 112, once an opportunity becomes closed, it is omitted from the following day's feed of opportunities and will be physically deleted from the pharmacy management system mainframe 140. Once this occurs, then the data would not be available to be displayed on the POS system 114. In order for opportunities that are closed to be displayed on the POS system 114 outside of the same day, the queries of the opportunity system 250 may have logic to keep sending these opportunities (e.g. a query may decide to re-send a closed opportunity if the only action chosen was "Patient unavailable"—then the POA system will still see and display the opportunity).

Configuration Portal 180

The configuration portal 180 provides the capability to setup and to manage the configurations of programs and opportunities through a simple interface. For example, the configuration portal 180 provides a user 190 with the capability to search for programs currently defined. The user 190 will be able to search based on the program description for user levels defined for the user level for pharmacists (opportunities will only be displayed to a pharmacist) or the user level defined for all users (opportunities will be displayed to all users). The search may also be based on the suppression type. The search results will display programs that match the search criteria or all programs if no search criteria were used. For each program, the following fields may be displayed:

Program Id
Program Description
User Level
Suppression Type
Last User ID
Last Updated Date The configuration portal 180 may also provide a user with the capability to add a new program. To add a user level, the user provides a program description, a user level (e.g., pharmacist or all users), and suppression type. The suppression type at a program level allows the user to suppress opportunities for a customer during the dispensing flow. The values are populated based on the configuration selection.

The configuration portal 180 may also provide the capability for a user to edit an existing program. From the program search screen, the user selects an existing program for update. This will take the user to the program setup screen where the fields will be displayed for update. The user may edit the program description, the user level, and the suppression type. The values again are populated based on the configuration selection. If an existing suppression value is removed, a warning will be displayed and the underlying values will be cleared from the table.

The configuration portal 180 also permits actions to be assigned or unassigned to a program. A minimum of one assigned action is required or a warning will be displayed. All available actions may be displayed with a checkbox on the left to indicate whether an action has been assigned or unassigned for a program. To add a new action, a blank Action Setup Screen may be launched.

The configuration portal 180 also enables web links to be assigned or unassigned to a program. All available web links may be displayed with a checkbox on the left to indicate whether a web link has been assigned or unassigned for a program.

The configuration portal 180 further enables the user to add opportunities for an existing program. An add icon allows the user to add an opportunity by launching the Opportunity Setup Screen. The fields available for user entry include the Opportunity Description, Priority (e.g., value 1-99), and Suppression Value(s). The suppression values at an opportunity level allow the user to suppress opportunities for a customer during the dispensing flow. The values are populated based on the configuration selection.

All available configurations are displayed to the user. The user also may remove a configuration. The portal application 180 need not enforce any business rules as it relates to actions assigned to a program to which an opportunity belongs. The following fields can be added to configure an opportunity for a program:

Config Name/Type—values are populated based on the configuration selection, including Add Start by Date, Task Priority, Add Service Type, and Add Service Vaccine.

Config Value—values are populated based on the configuration selection.

The configuration portal 180 may further provide the capability to edit opportunities for an existing program. An edit icon allow the user to edit the opportunity by launching the Opportunity Setup Screen for the selected row. The parameters that may be edited include the Opportunity Description, Priority (e.g., values 1-99), and Suppression Value(s). The list is based on the program type selected, and multiple values may be selected.

The configuration portal 180 also provides the capability for a user to display existing actions. For each action, the Action Code and Action Description are displayed.

The configuration portal 180 further provides the capability to add actions outside the program flow. The fields available for user entry include the Action Description and the Action Code. The user may enter an action ID when adding a new action, but the action ID cannot be a duplicate of an existing action ID. The action ID may be used for sorting in the pharmacy management system 112.

Finally, the configuration portal 180 may also provide the capability for a user 190 to edit actions outside the program flow. However, the actions can only be unassociated from programs. The parameters that may be modified include the Action Description and the Action Code.

System Flow Chart

Figure 2:
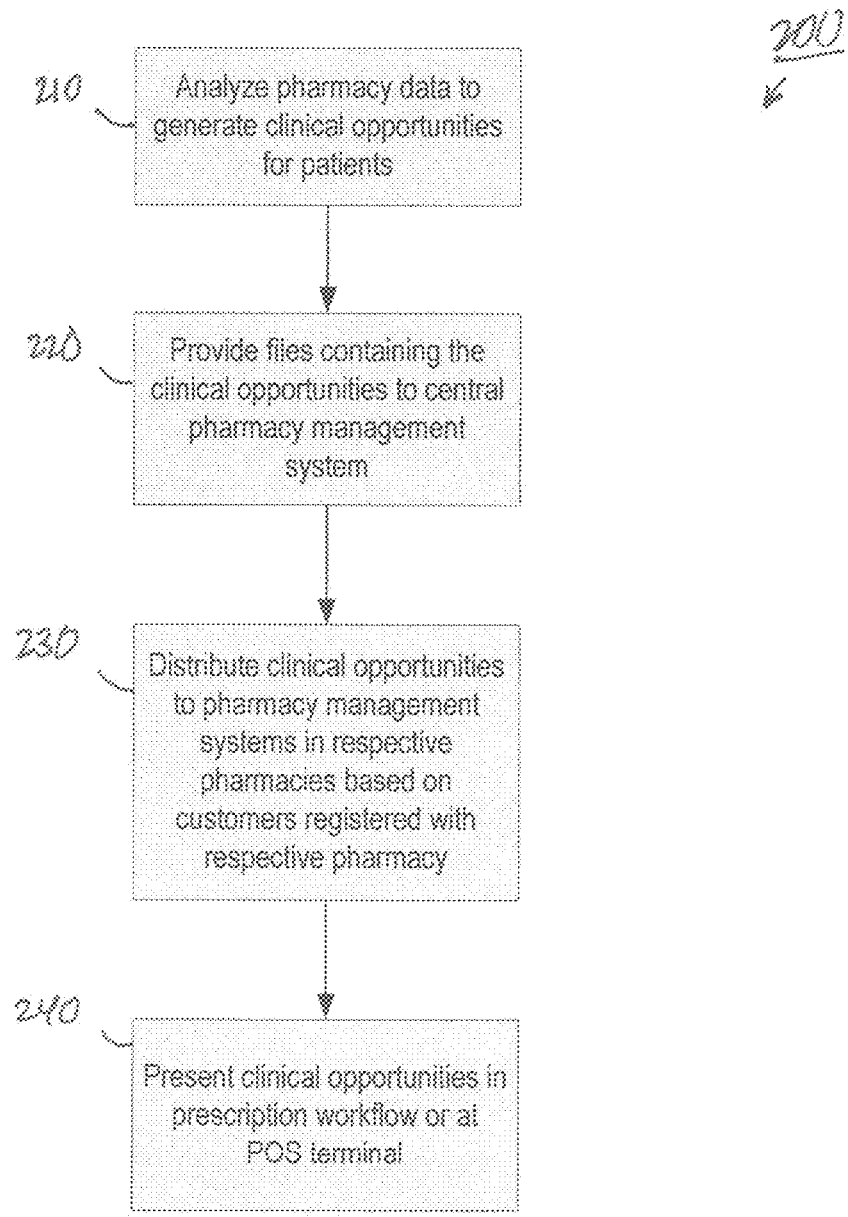
FIG. 2 illustrates a simplified flow chart of a method of presenting opportunities to a pharmacy management system in sample embodiments.

FIG. 2 illustrates a simplified flow chart of a method 200 of presenting opportunities to a pharmacy management system 112 in sample embodiments. As illustrated, the method includes analyzing pharmacy data to generate clinical opportunities for patients at operation 210, and providing files containing the clinical opportunities to a central pharmacy management system 140 at 220. The central pharmacy management system 140 distributes the clinical opportunities to pharmacy management systems 112 in respective pharmacies based on customers registered with each respective pharmacy. The clinical opportunities for a customer are presented during interactions with the customer in a prescription workflow when a pharmacist fills prescriptions using pharmacy management system 112 or a salesclerk or technician concludes a sale for a prescription at a Point of Sale (POS) system 114 in a pharmacy 110 at which the customer is registered. As noted above, in sample embodiments, the clinical opportunities may include an immunization, medication therapy management, performance measurement, predictive refill, and the like. Further details regarding the operation of the respective components are provided in the sample embodiments described with respect to FIG. 3 to FIG. 9.

Sample Embodiments

The system configures clinical programs and clinical opportunities that are to be presented for each patient. The data elements for the clinical programs may include the program ID, the program description, and user level values indicating whether the opportunities will only be displayed to a pharmacist or will be displayed to all users. The data elements for the clinical programs also may include suppression type values such as vaccine, service, national drug code (NDC), and GCSN, which are described in more detail below. On the other hand, the data elements for the clinical opportunities may include the opportunity ID, the opportunity description, priority, program ID, and suppression value. Configurable elements for the clinical opportunities may include, for example, Add Task Screen, Print Forms Screen, and Add Service Screen. Add Task Screen includes a "start by" date for a generated task (# of days from current time) and a default of zero (current time), as well as a "priority" for a generated task (High/Medium/Low). The default priority is high. The service (e.g. "vaccine" field) may be pre-selected on the Add Service Screen when launched via actions.

In sample embodiments, a new screen is created within the pharmacy management system to display and to take action on available opportunities. The patient related data elements listed below are displayed at the top of this screen. These data elements also may be shared with the Medication History screen in the pharmacy management system:
  Name
  Address
  Phone
  Date of Birth
  Gender
  Compliance/Adherence Score (if available)
  OTR Contact Number (if available)
  OTR 1st Target Date (if available)
  OTR 2nd Target Date (if available)

A list of currently available opportunities for a patient will be displayed based on priority. The number of opportunities to be displayed at a time is configurable. For each opportunity, the following data elements may be displayed:
  Program Name
  Opportunity Description
  User Action Taken Flag
  Last User to Take Action
  Time of Last User Action Taken
  Etc.

All available actions for the selected opportunity may be displayed. The list of actions will for each program is predefined. For each action, the following data elements may be displayed:
  "Perform Action"! "Undo Action" image button
  Action Description
  Last User to Take Action
  Time of Last User Action Taken The clinical opportunities screen may also contain a section for the user to enter comments. Comments entered will be specific to each opportunity rather than tied to a single action. Only one set of comments are kept for each opportunity, meaning that a second user viewing the opportunity will see the first user's comments and any changes to the comments by the second user will update or overwrite comments made by the first user.

Portal links also may be available on the clinical opportunities screen for all opportunities and can be configured at a program level. If no opportunities are configured for the current program(s), then the "portal links" button will not be displayed. Sample portal links include:
  State Immunization Registry (where applicable)
  Vaccine Central (results from external source)
  Outcomes MTM
  EQuIPP (pharmacy benchmark performance tool)

Figure 3A:
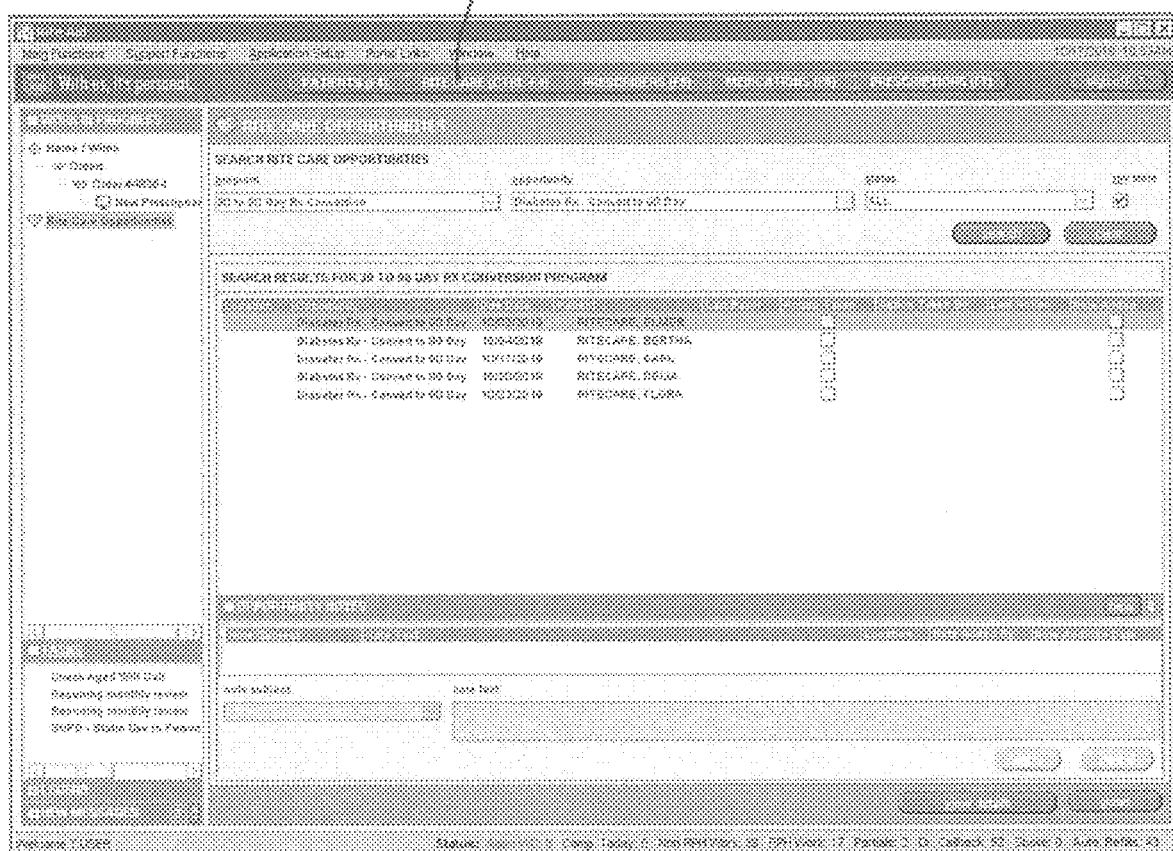
FIG. 3A illustrates a clinical opportunities search screen including a button available in the top menu bar to allow the users to access the clinical opportunity search screen.

The pharmacy management system may be modified to create a new screen to allow the user to search clinical opportunities available at their store. For example, FIG. 3A illustrates a clinical opportunities search screen 300 including a button 310 available in the top menu bar to allow the users to access the clinical opportunity search screen. This button 310 may be added between the patient search and doctor search buttons. In sample embodiments, the user may search clinical opportunities based on the following criteria:
  Program Type
  Opportunity Type
  Status The search will display opportunities for the store housing the pharmacy management system that match the search criteria. The opportunities for that store may be filtered. For example, all immunizations available for that store may be identified. For each opportunity, the following data elements may be displayed:
Opportunity Description
Patient Name
Last Payor
User Action Taken Flag
Last User to Take Action
Time of Last User Action Taken
Etc.

In a sample embodiment, the clinical opportunities may be launched from the clinical opportunity search screen. A 'view details' button may be added to the search screen. A user will be able to select an opportunity displayed in the search result by selecting a 'view opportunity' button or by double-clicking the opportunity to launch the Clinical Opportunity screen. When the user launches the Clinical Opportunity screen from the search results, only the selected opportunity may be displayed. If the user launches the screen from the search results screen and chooses to create a script for the selected opportunity, then the user will first have to select the order in which the script needs to be added.

In sample embodiments, the search screen may include a location column that shows the store location, a due date column, a 'My Store' checkbox that may be checked to show the store's current opportunities, an opportunity notes section, and a drop down box that lists opportunity notes to select from. The search screen also may have editable text and a timestamp of the note written. Activity documented on the search screen by any user will not result in the action status of the opportunity moving to pending or closed status.

Figure 3B:
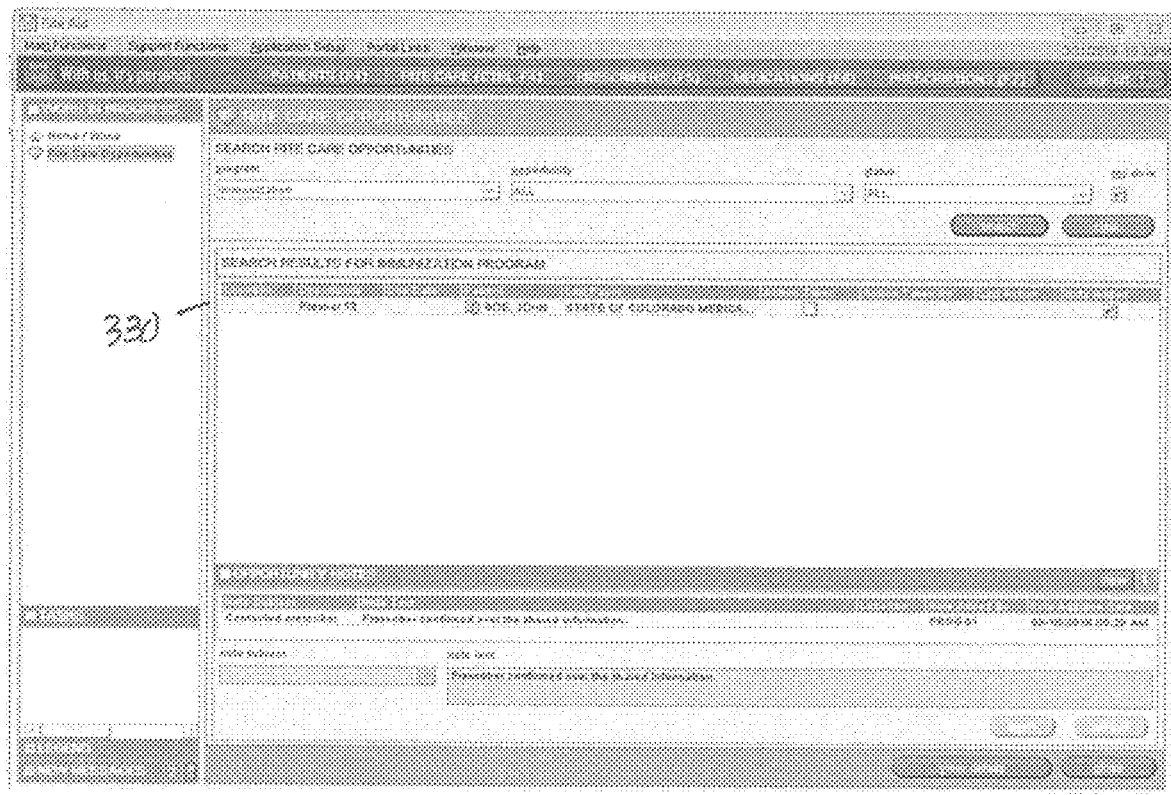
FIG. 3B illustrates a clinical opportunities screen that may be displayed during the dispensing workflow of the pharmacy management system if the selected patient has available opportunities.

The clinical opportunities screen 320 illustrated in FIG. 3B may be displayed during the dispensing workflow of the pharmacy management system if the selected patient has available opportunities. After a user has selected a medication, the clinical opportunities screen 320 may be automatically launched over the order wizard. At this point in the dispensing flow, only opportunities 330 that are in a "New" status will be displayed. When the user opens a prescription in product review status, then the clinical opportunities screen will be automatically launched over the order wizard. At this point in the dispensing flow, any opportunities that are in pending, unacted upon by the technician, or configured only to the pharmacist will be displayed. However, if there are high priority notes for the current prescription, then the high priority notes must display before the clinical opportunity screen is displayed. The auto-launch of the opportunity screen may be configurable.

In sample embodiments, a clinical opportunity may be suppressed during dispensing flow if a prescription being dispensed is to address that opportunity. Suppression types may be configured for a program or an opportunity. As noted above, available suppression types may include vaccine, service, NDC, and GCSN. The suppression value should be of the same type as the suppression type setting on the program for the opportunity. For example, if the suppression type for the immunization program is set to vaccine and the suppression value for an immunization opportunity is set to 'FLU', then this opportunity will not be displayed while dispensing a prescription for a flu vaccine.

The rules for suppressing an opportunity depend on suppression type and suppression value. For example, suppression type "Vaccine" suppresses the opportunity for all prescriptions where the NDC is for a particular vaccine. Similarly, suppression type "Service" suppresses the opportunity for all prescriptions where the NDC is for a particular service, the suppression type "NDC" suppresses the opportunity if the prescription being dispensed is for the particular NDC, and the suppression type "GCSN" suppresses the opportunity if the prescription being dispensed is for the particular GCSN.

Figure 4:
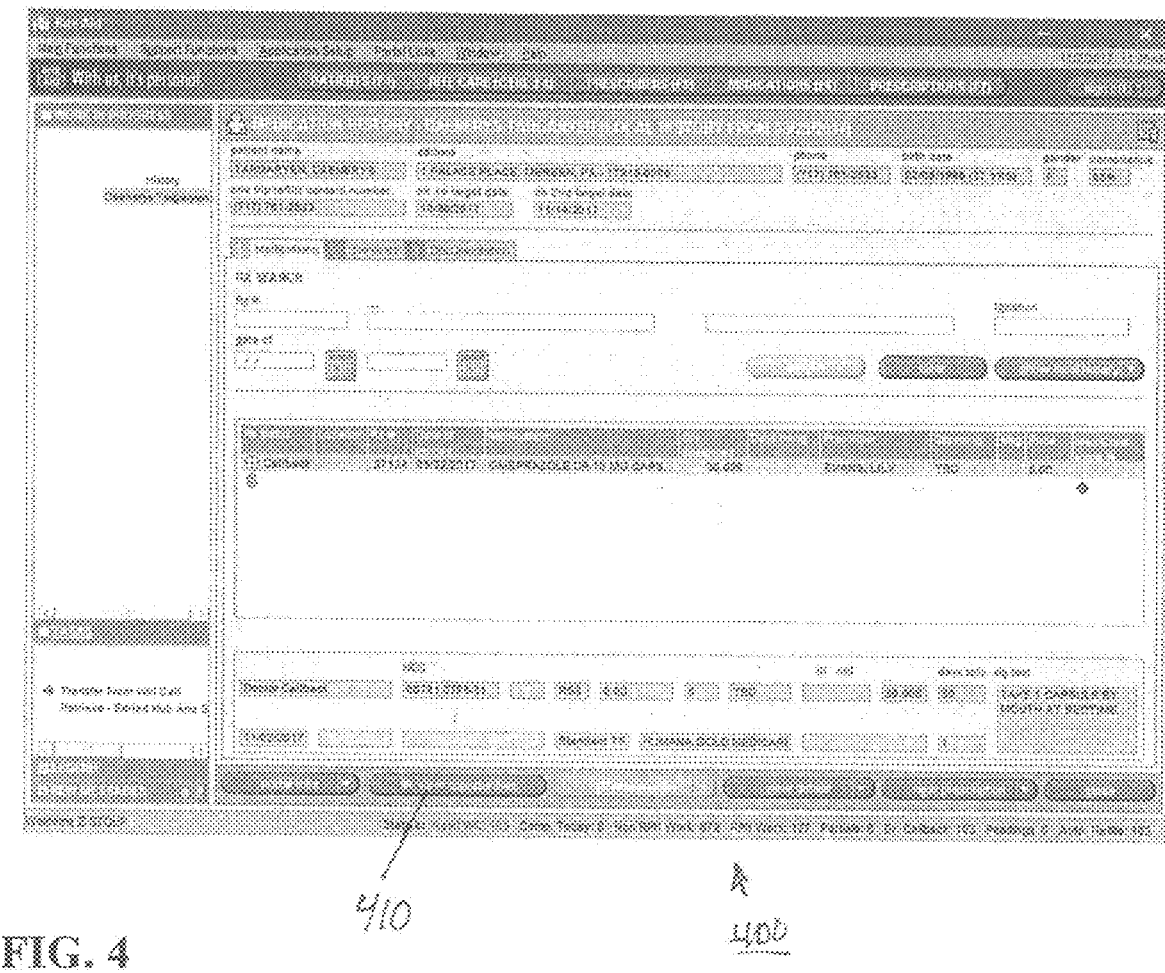
FIG. 4 illustrates the Medication History screen modified to include a new "View Opportunities" button.

In sample embodiments, a dedicated button is added on the Medication History screen of the pharmacy management system for use in launching the Clinical Opportunities screen for the patient. For example, as illustrated in FIG. 4, the Medication History screen 400 may be modified to include a new "View Opportunities" button 410. This button will be enabled only if there are opportunities for the selected patient. If the user launches the screen from the Medication History screen and chooses to create a prescription for the selected opportunity, then the user may first have to select the order in which the prescription needs to be added.

Figure 5:
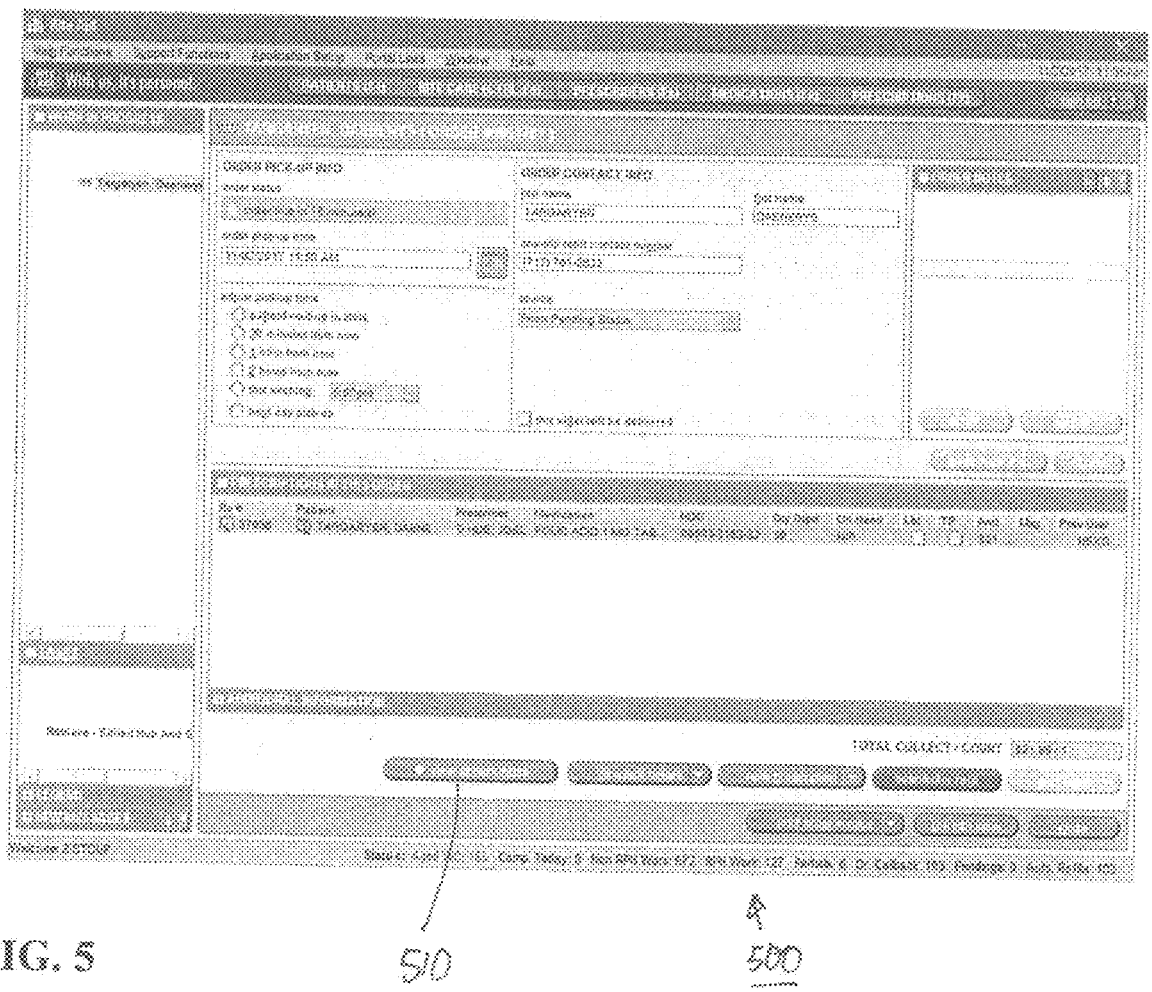
FIG. 5 illustrates the Order Summary screen modified to include a new "View Opportunities" button.

The Clinical Opportunities screen may also be launched from the Order Summary screen in the pharmacy management system by adding a dedicated button on the Order Summary screen to launch the Clinical Opportunities screen for the patient. As illustrated in FIG. 5, the Order Summary screen 500 may be modified to include a new "View Opportunities" button 510.

If the user chooses to create a prescription for the selected opportunity, then the prescription is added to the current order. All opportunities are either New, Pending, Closed, Deleted, or Removed as outlined below. New or Pending opportunities are available for users to take action upon whenever they are displayed.

New
An opportunity is considered new when an action has not been performed yet. "New" is the state of any new opportunity that is created for a patient. If an opportunity was previously in Pending status and has had all of the actions taken on it undone by either a technician or a pharmacist, then the opportunity may become "New" again.

Pending
An opportunity is considered "Pending" when an action has been performed by a technician but not yet reviewed by a pharmacist.

Closed
An opportunity is considered "Closed" when a pharmacist has taken an action or reviewed an action taken by a technician.

Deleted
An opportunity is considered "Deleted" if it was in a Pending state but it does not come back in the subsequent search because it is no longer valid for the patient.

Removed
An opportunity is considered "Removed" if it was in a "New" state but it does not come back in the subsequent search because is no longer valid for the patient.

The pharmacy management system is adapted to control how opportunities for a patient are displayed to the user on the Clinical Opportunities screen. For example, the number of opportunities displayed at one time is limited. In sample embodiments, a configuration flag determines the maximum number of opportunities to be displayed during the dispensing flow. When a pharmacist is opening the Clinical Opportunities screen and a technician has responded to opportunities for the patient, then those opportunities will always be displayed to the pharmacist at product review. Additionally, the pharmacist may be shown new opportunities if they are higher priority than those that the technician responded to (e.g. new opportunities arrived via daily feed since the technician last worked the prescription).

On the other hand, opportunities will not be displayed when the prescription being dispensed does not belong to the current store. For example, during shared data entry at a helping store, no patient opportunities will be presented. Also, opportunities may not be displayed when product review is done for a spoke prescription at the hub or at the central fill facility.

Opportunities that are closed, deleted and removed will not be displayed on the Clinical Opportunities screen.

If Clinical Opportunities are displayed for a patient during the dispensing flow once for each touch point (i.e., at select medication and product review) in a store, opportunities will no longer be auto-launched for that patient in that store for rest of that day for the same touch point. In other words, the same opportunities do not keep popping up on the Clinical Opportunities screen.

When configuration data is missing, the opportunities/actions will not display. In sample embodiments, the following data elements must be defined in order for opportunities to be displayed in the pharmacy management system:
Program name;
Opportunity name; and
At least one allowed action in the program configuration table (RXCPC) for the program ID to which the opportunity belongs. Of the allowed actions defined, only those which also have the action text defined may be displayed. Since an action text is a required field when creating an action, if none of the configured allowed actions have an action text defined, then the opportunity may not be displayed at all.

By design, if the above configuration data is missing, then an opportunity or action may not be displayed. However, as long as the program and/or opportunity descriptions are present in the definition tables, the program/opportunities will appear in the Clinical Opportunity search dropdown menus.

To determine whether an action was taken from the search or workflow function and what opportunities were presented from the workflow, the list of opportunities shown to the user in the dispensing workflow may be captured to allow reporting to be performed. The opportunities may be displayed for an action to be taken. The data from such an audit may be forwarded to the opportunity system and/or stored in the pharmacy management system mainframe.

The user is allowed to perform actions on available Clinical Opportunities for a patient. For example, the table below lists representative actions that a user may take in order to respond to an opportunity, along with the corresponding event that would be triggered in in the pharmacy management system. The list of actions available and the action display text for a particular opportunity may be configured through the portal application.

| Action ID (Used for Display Order) | Proposed Action Display Text | System Action When Performed | Programs Configured to Display Action |
|---|---|---|---|
| 100 | Start Rx | Launch the Order Wizard to create a new prescription for the patient. If the Clinical Opportunity screen was launched during the dispensing flow or from Order Summary, the new script will be created in the same order and will open in the background to be completed after the current prescription. If the screen was launched from Medication History or the Opportunity Search screen, the user will have to select an order or create a new order before the script can be created. Once the prescription is created, an Rx Note will be automatically added to it stating that the script was created as a result of a clinical opportunity, along with the opportunity description. | Immunization |
| 200 | Create patient follow-up task | Launch the Task Wizard to allow the user to add a reminder task. The user will have to choose the appropriate task category. The following data will be pre-populated:<br>1. Category: Clinical Opportunity;<br>2. Description: <Opportunity Description>;<br>3. Action required: Press F9 to view patient profile. Contact SSCUSTVIEW$$ at $$CUSTPHN$$ and discuss the recommended vaccine (Prevnar 13). \n\nDocument outcome as appropriate (i.e., Start Rx, Log Self-Reported Immunization). Discuss clinical opportunity and educate as needed\n4. Document clinical opportunity outcome as appropriate (New Rx, Services tab, MTM platform)";<br>4. Priority: High, Medium, or Low as specified in opportunity configuration;<br>5. Start By: Current time plus number of days specified in opportunity configuration (default is current time);<br>6. Due by: Start By time + 1 week;<br>7. Expires on: 11:59pm on Due By date. | All Programs |
| 300 | Patient not interested | No system action occurs when the user selects this choice. | Immunization MTM Predictive Refill |
| 400 | Log self-reported service | Launch the Service Wizard to allow the user to document the service. The service type and specific service will be pre-populated (e.g. "Immunization" and "Influenza" will both be pre-populated). | Immunization |
| 500 | Enroll patient in refill service | Launch Customer Wizard with the Demographics tab selected. | Predictive Refill |
| 600 | Print Point of Care paperwork | The action will result in Point of Care paperwork being printed for the patient. If the Clinical Opportunity screen was launched during the dispensing flow, the paperwork will be printed when the prescription is post-finalized. In all other scenarios, the paperwork will be printed immediately. | Performance Measurement |
| 700 | Print form(s) | Launch the Print Forms screen. If a form name is specified in the opportunity configuration, then | Not Configured |

| Action ID (Used for Display Order) | Proposed Action Display Text | System Action When Performed | Programs Configured to Display Action |
|---|---|---|---|
| 800 | Patient un-available | that form will be pre-selected from the "report type" dropdown. An Order Note will be added to the order (dispensing flow only) with the title "Clinical Opportunity" and description "Monaco Bag Index Card for Opportunity Descriptions" | Immunization MTM Predictive Refill |
| 900 | Log in to platform using 'portal links.' | No system action occurs when the user selects this choice. | MTM |
| 1000 | Defer to pharmacist | No system action occurs when the user selects this choice. | Immunization Performance Measurement Predictive Refill |

Note:
The above table lists the proposed action display text and it can be changed as desired.

All allowed actions for a program may be sorted in the pharmacy management system based on their Action IDs. Lower action IDs may be located at the top of the screen. Action IDs are not re-used/recycled once they have been issued. The initial Action IDs in the table above have been spaced by intervals of 100 to allow adding new actions in any order.

During the dispensing flow, at least one action must be completed on at least one available opportunity that is presented before the screen can be closed. This requirement is configurable. Outside of the dispensing flow, the user may cancel out of the screen without performing any action.

A button may be present next to each action that when clicked, will perform the action. An action cannot be performed a second time unless it is first undone by the user. The same button that is used to perform an action may be used to undo the action after it has been performed. Undo can only be performed as long as the opportunity has not been closed. A user can undo any action that they themselves have performed.

A pharmacist can undo an action performed by a technician. Except for a pharmacist being able to undo an action taken by a technician, a user cannot undo an action taken by another user. To the user, undoing an action may simply be a visual indicator. Any systematic result of the action, such as creating a new prescription, new task, etc. may be undone by the user in addition to undoing the action on this screen. When an action is undone, a note may be displayed at the bottom of the screen explaining this to the user. As soon as any other action is performed again, the note may be hidden.

If a technician performs an action during the dispensing flow and later wishes to undo the action, the Clinical Opportunities screen may be opened for the patient outside of the dispensing flow to undo the action as long as the opportunity has not been closed. A pharmacist may undo their own action before the Clinical Opportunities screen is closed. Once the screen is closed, the action is final and the opportunity is placed in a closed state. If all actions are undone by either a technician or pharmacist, then the opportunity will become New again.

In sample embodiments, transactions by the pharmacy management system are immediately updated to the pharmacy management system mainframe. At intervals (e.g. 30 minutes), the pharmacy management mainframe synchronizes with the respective pharmacy management systems to provide information relating to a new customer, opportunities, and the like. An opportunity that has been acted upon in one store will not be displayed to a user in another store after the synchronization process has moved the data to all stores where the patient subscribed. If a user opens an opportunity prior to another store's actions synchronizing to their store and attempts to perform an action on it, then the pharmacy management mainframe will respond with an error indicating that the action has already been performed at another store and the user must cancel.

Figure 6:
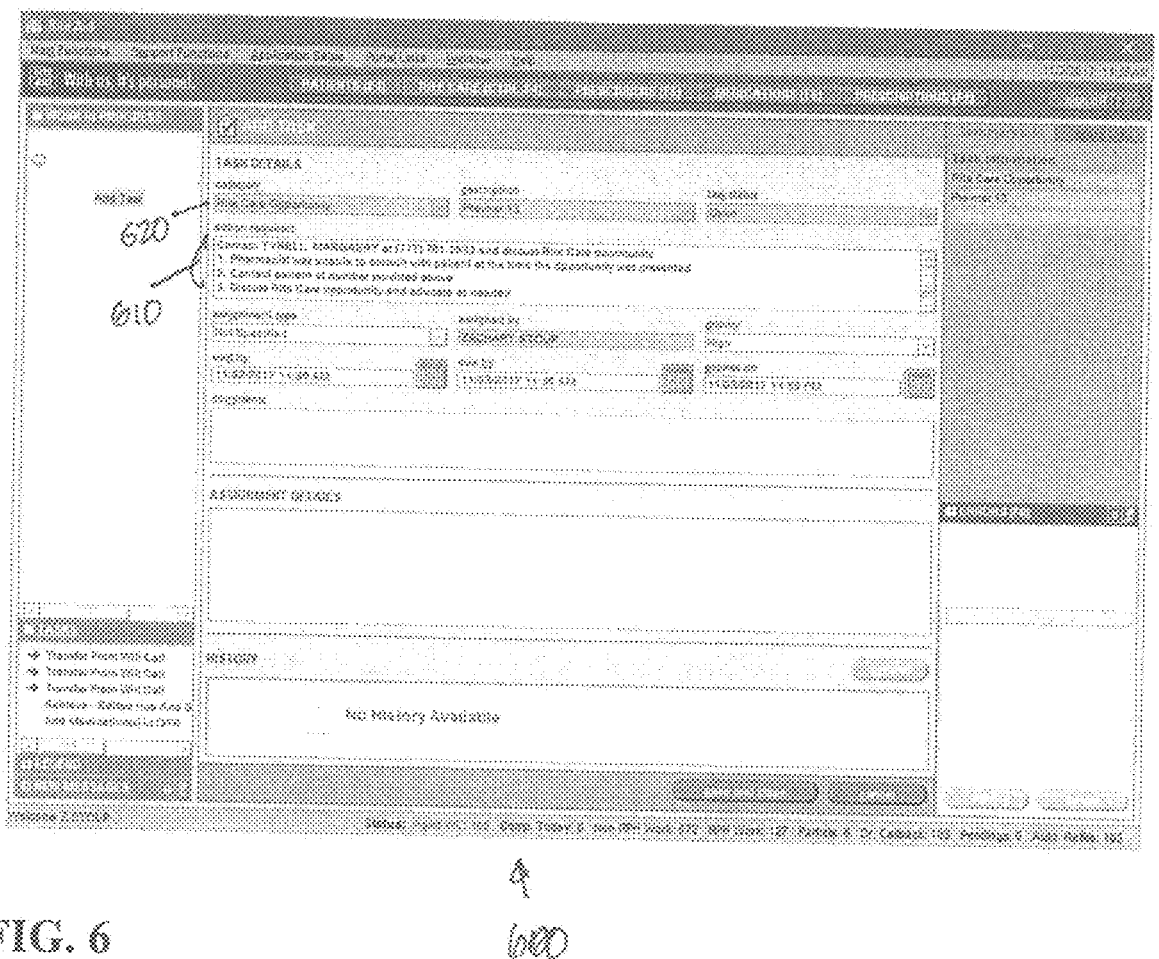
FIG. 6 illustrates the screen for the Add Task Wizard pre-populated with data based on the clinical opportunity when launched from a new screen.
Figure 7:
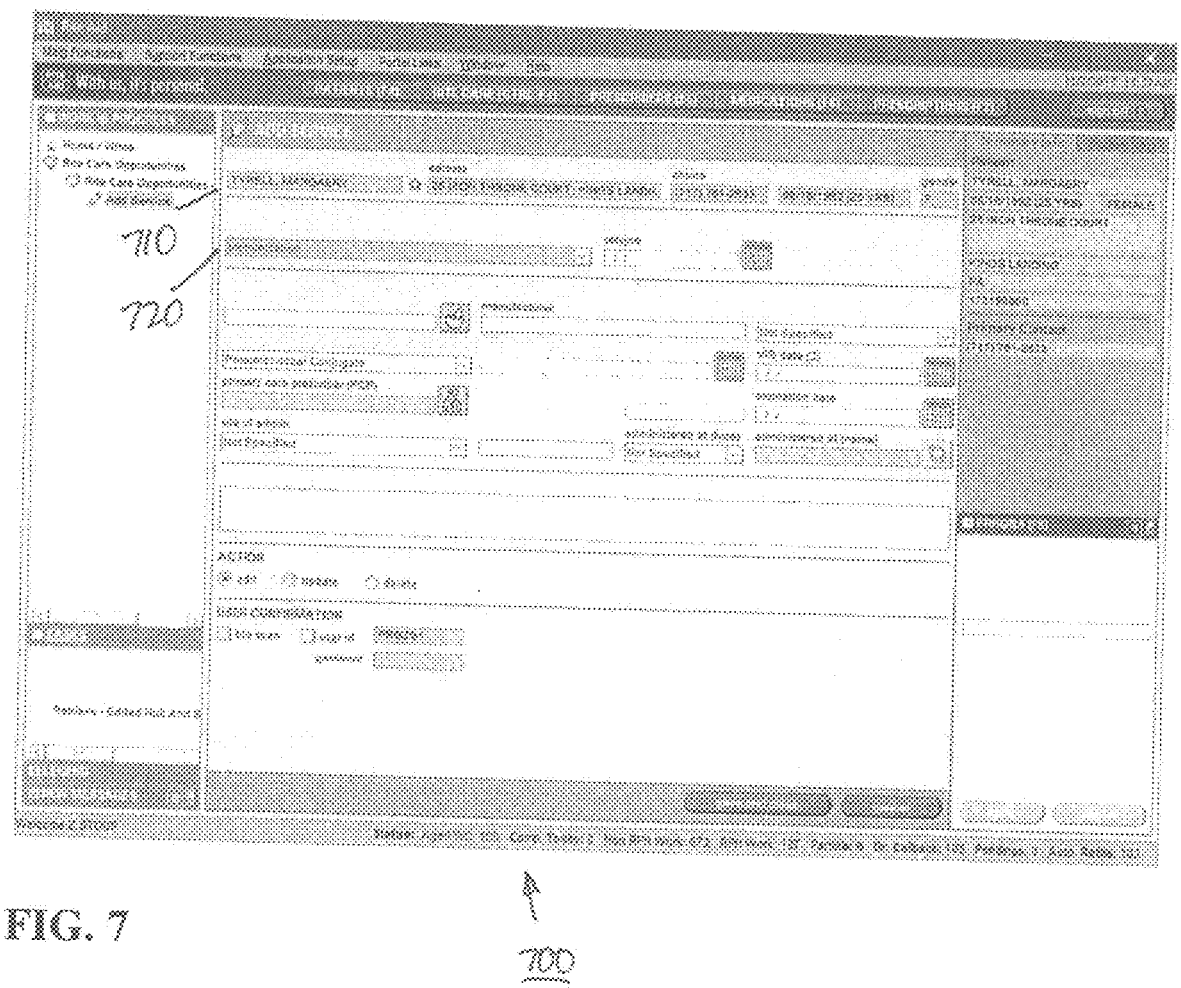
FIG. 7 illustrates the screen for the Add Service Wizard prepopulated with data based on the clinical opportunity when launched from a new screen.

When the user responds to a clinical opportunity by selecting an action that results in launching the Add Task Wizard, a new task category is added so that the user may create an appropriate task related to the clinical opportunity. As illustrated in FIG. 6, the screen 600 for the Add Task Wizard may be pre-populated with data 610 based on the clinical opportunity 620 when launched from the new screen. Similarly, as illustrated in FIG. 7, the screen 700 for the Add Service Wizard may be prepopulated with data 710 based on the clinical opportunity 720 when launched from the new screen. Every opportunity that allows a task to be created through one of its allowed actions also has a corresponding task description defined that matches the opportunity ID/description. This task description is pre-selected when the Add Task screen launches. For example, a new task in the dispensing application of the pharmacy management system may be, triggered based OD the selected action.

The ability to turn-off the entire clinical functionality also may be provided in the pharmacy management system. For example, the ability to turn-off the auto-launch of the clinical opportunity feature in the pharmacy management system may be provided from the Medication Select point, Product Review point, or both. In other words, any pop-up functionality for the clinical opportunities may be disabled. The ability to disable the requirement that a user must perform an action during the dispensing flow at the Medication Select point, Product Review point, or both may also be provided.

Figure 8A:
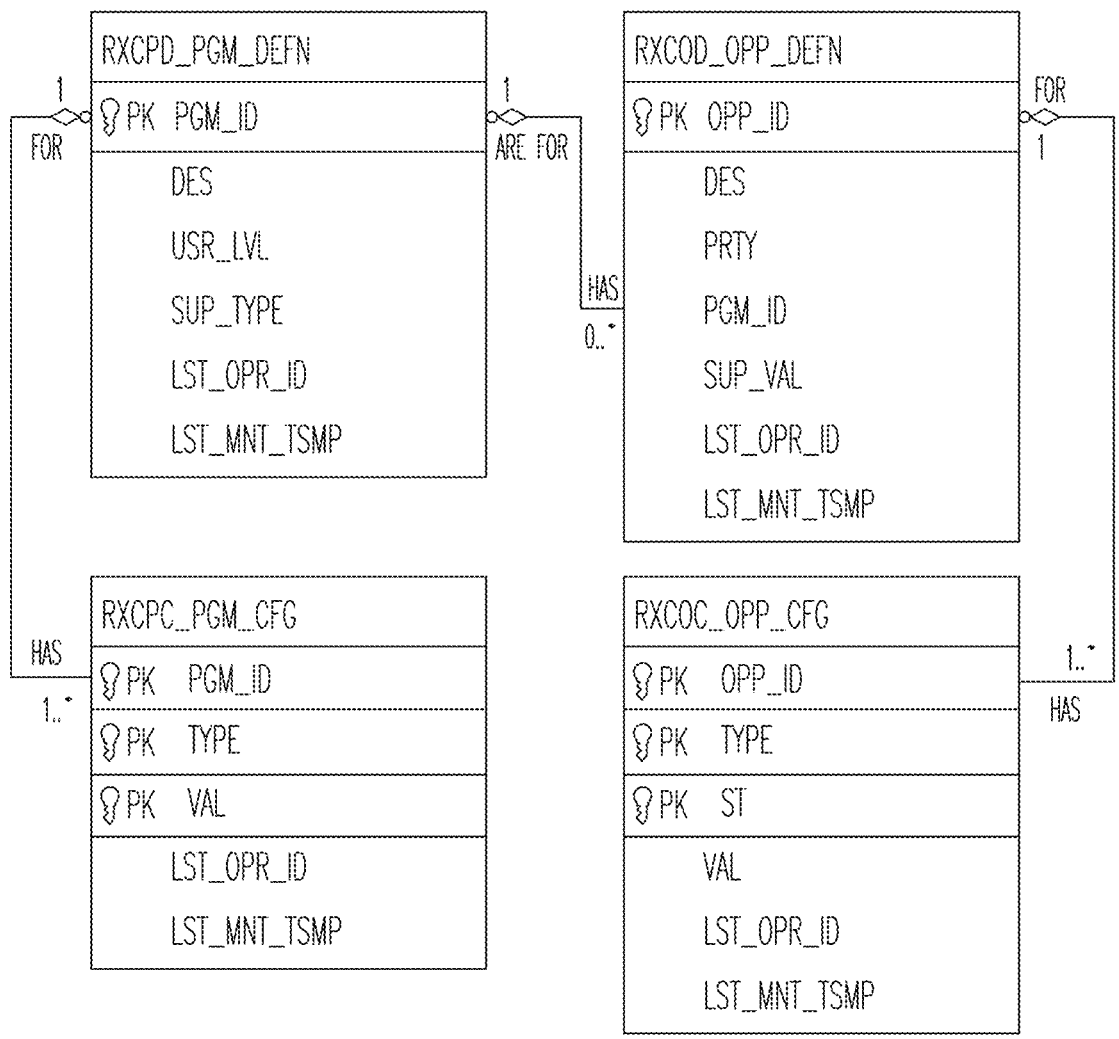
FIG. 8A and FIG. 8B together illustrate the database design for the pharmacy management system mainframe in a sample embodiment.
Figure 8B:
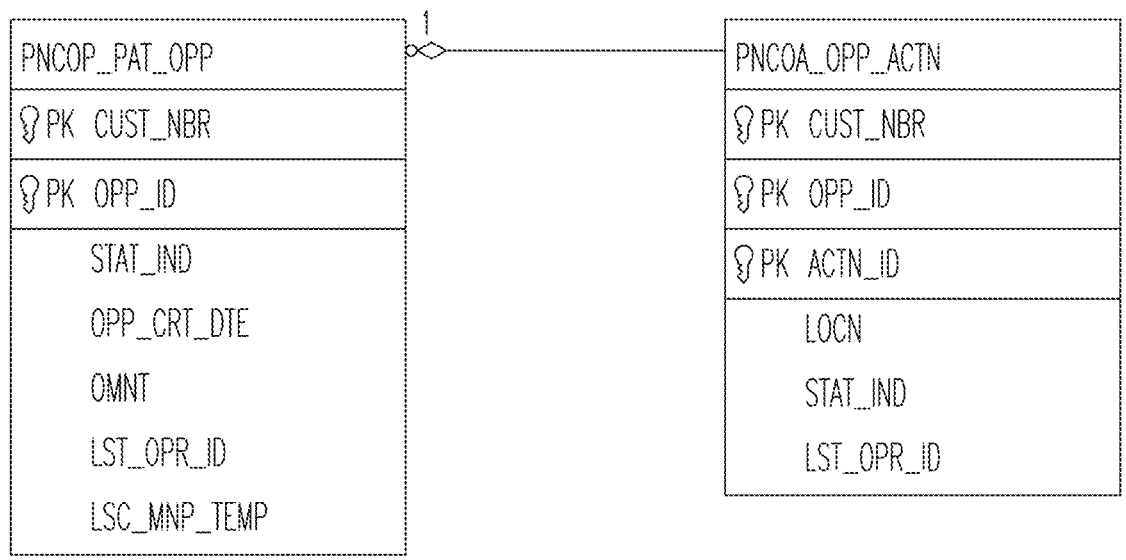

In sample embodiments, the pharmacy management system mainframe includes corresponding client database tables that are linked by program opportunity ID. The following tables are illustrated in FIG. 8A and FIG. 8B, which illustrate the database design for the pharmacy management system mainframe. As illustrated in FIG. 8A and FIG. 8B:

A table RXCPD PGM DEFN assigns a unique ID and name to all programs. It also contains other attributes of a program such as user level, suppression type, etc.

A table RXCOD_OPP_DEFN assigns a unique ID and name to all opportunity types within a program ID, as well as defining other attributes of the opportunity, such as its priority ranking.

A table RXCPC PGM CFG assigns possible types for a program like "allowed actions" or "weblinks."

A table RXCOC_OPP_CFG holds configuration values at the opportunity level. Examples include the form name to pre-populate upon selecting the "Print form(s)" action and the service type to pre-populate upon selecting the "Patient already has received the service" action.

The table PNCOP_PAT_OPP contains all patient-specific opportunity records that have been generated by the opportunity system.

The table PNCOA_OPP_ACTN uses a one-to-many relationship to store all available user actions and the responses to each for every patient-level opportunity.

The opportunities are refreshed every day with data from the opportunity system. As opportunities reach their expiration date, they will no longer be sent from the opportunity system and they will be deleted from the pharmacy management system database at the store and at the mainframe. In accordance with current rules for pharmacy data retention, recorded actions taken will be present on the opportunity system for three years. The opportunity system may use this data for future calculations of opportunity eligibility.

Mainframe-Pharmacy Synchronization

As noted above, the pharmacy management system 112 may be implemented as the NexGen Pharmacy Management Application implemented by Rite Aid Corporation. In sample embodiments, the pharmacy management system 112 may synchronize data with the central pharmacy management system 140 via Wide Area Network (WAN) 195. A data synchronization process is used to synchronize data from the database 165 to the local pharmacy database of the pharmacy system 112. Since the local pharmacy database stores a copy of certain data, the synchronization process ensures that the local copy is current and that the local copy matches the master record stored in the central database 165. The synchronization process may be specific to data used by the pharmacy management system 112 located at the pharmacy 110.

Since the local pharmacy database includes only a subset of the data stored centrally, data subscriptions enable the synchronization process to determine which pharmacies 110 care about which data. Tables are used to map customers/addresses/doctors ("objects") to one or more pharmacies 110. This mapping is called a "subscription" (e.g. "Pharmacy X is subscribed to object A."). In sample embodiments, the data subscriptions may be at a location level or an object level and map data to one or more pharmacies 110. For example, the subscription data may be stored in tables including:

RXCSC—Customer Subscription table
RXCSA—Customer Address Subscription table
RXDSD—Doctor Subscription table
RXVLL—Location Level table Subscriptions may be added at the time of data extraction or when an online transaction has occurred that indicates that a pharmacy 110 has placed an object in its local database. Examples of such online transactions include specific customer selection, doctor selection, customer medication history inquiry, customer update, doctor update, address update, and the like.

The tables of the database 165 may further include a primary synchronization table (RXSYN_SYNC_TBL) that may be used by a mainframe batch sync process when a "real-time sync push" fails. A secondary synchronization table (RXSYT_SYNC_TBL) also may be used that includes rows that are fetched only after there are no rows remaining on the RXSYN_SYNC_TBL. The secondary synchronization table is used by processes that produce potentially large amounts of table inserts/updates/deletes. Sync XML, is placed on this table and the table updates are bypassed in the normal batch sync process. RXSYT is used to avoid negative impact on the normal dispensing type data that needs to synchronize to the pharmacies 110 in a timely manner. Usage of this table also reduces synchronization network traffic.

In sample embodiments, the data synchronization may be based on location. The Location Level table RXVLL provides the data location information.

The protocol implemented by the central pharmacy management system 140 includes execution of a batch synchronization job at periodic intervals. For example, a batch synchronization job may be executed every thirty minutes. The batch synchronization job inserts rows into a new primary synchronization table (RXSYN) where one row is provided per database event per object/pharmacy mapping.

On the other hand, an online synchronization transaction may be initiated by the client at the pharmacy 110. The transaction may be executed at period intervals, such as every thirty minutes. The pharmacy 110 acknowledges receipt of rows from prior synchronization transactions, and the central pharmacy management system 140 deletes acknowledged rows and returns the rows remaining on RXSYN for that pharmacy 110. The received rows may be ordered by timestamp. Also, if a pharmacy 110 receives a synchronization record that does not make sense (e.g., an update to a row it does not have), the pharmacy 110 may do a complete refresh on the underlying object.

The batch jobs implemented by the central pharmacy management system 140 include processes for data synchronization, data synchronization problem reporting, synchronization of acquisition data, and the like. For example, a first job may pull records from a master log starting from the previous run of the first job, eliminate log records that represent a delete from the system, and process the remaining log records. In sample embodiments, the master log may contain the following fields or data:

Creator
Table Name
Time Stamp
Change Type (I)insert, (D)delete and (U)update
(U)pdate Type (B)efore and (A)fter
Load data for that table The synchronization records are inserted into RXSYN. The RXSYN inserts are either based on subscriptions or sent to one or all pharmacies 110.

The synchronization process also may be split into multiple jobs running in parallel with each job handling a subset of the synchronized tables. Each successive run of the master log extraction schedule is identical; it picks up where the previous job left off.

Data synchronization problem reporting may use RXSYN to hold synchronization records with rows written by the batch synchronization process that fetches and deletes rows during execution of synchronization transactions. The synchronized records may be collected by the pharmacies 110 at the periodic synchronization intervals (e.g., every thirty minutes). Outdated records may be an indication of a possible problem with pharmacy's synchronization service. A job may check RXSYN and submit a report when outdated RXSYN rows are found.

A batch process also may be used to process changes made by an Acquisition Program. A control card may indicate which programs modified data, and the data modified by these programs may be excluded from the synchronization process in accordance with timestamps determined within the Acquisition Batch Process.

The central pharmacy management system 140 also may include tables that indicate the restart point in each batch synchronization program by job and program in accordance with the last recorded timestamp. The tables are updated with the last transaction timestamp after data is committed.

Data synchronization tables also may be populated from a master log utility that indicates the start and finish of the utility and the starting and ending timestamp processed during that time. A further table may contain the total number of Insert, Delete and Update statements for each table obtained from the utility.

On the client (pharmacy) side, the protocol may include a synchronization service on a server in the pharmacy 110 that sends requests to the central pharmacy management system 140 to receive sync records from RXSYN. The service may be restarted daily at the pharmacy 110. At startup, the service determines sleep time adjusted by load balancer logic of the central pharmacy management system 140 so that each pharmacy 110 does not contact the central pharmacy management system at the same time. After sleep time, the service creates a sync request to send to the central pharmacy management system 140. The request may include acknowledgements of previous sync records received and processed from the central pharmacy management system 140. The central pharmacy management system 140 deletes acknowledged rows and returns the rows remaining on RXSYN for that pharmacy in a sync response. The rows are ordered by timestamp. The service also deletes sent entries that have been acknowledged. The service also applies all other updates by updating underlying database data and adds a record of each update to a table of acknowledgments of previous sync records.

Lifecycle of an Opportunity

Figure 9:
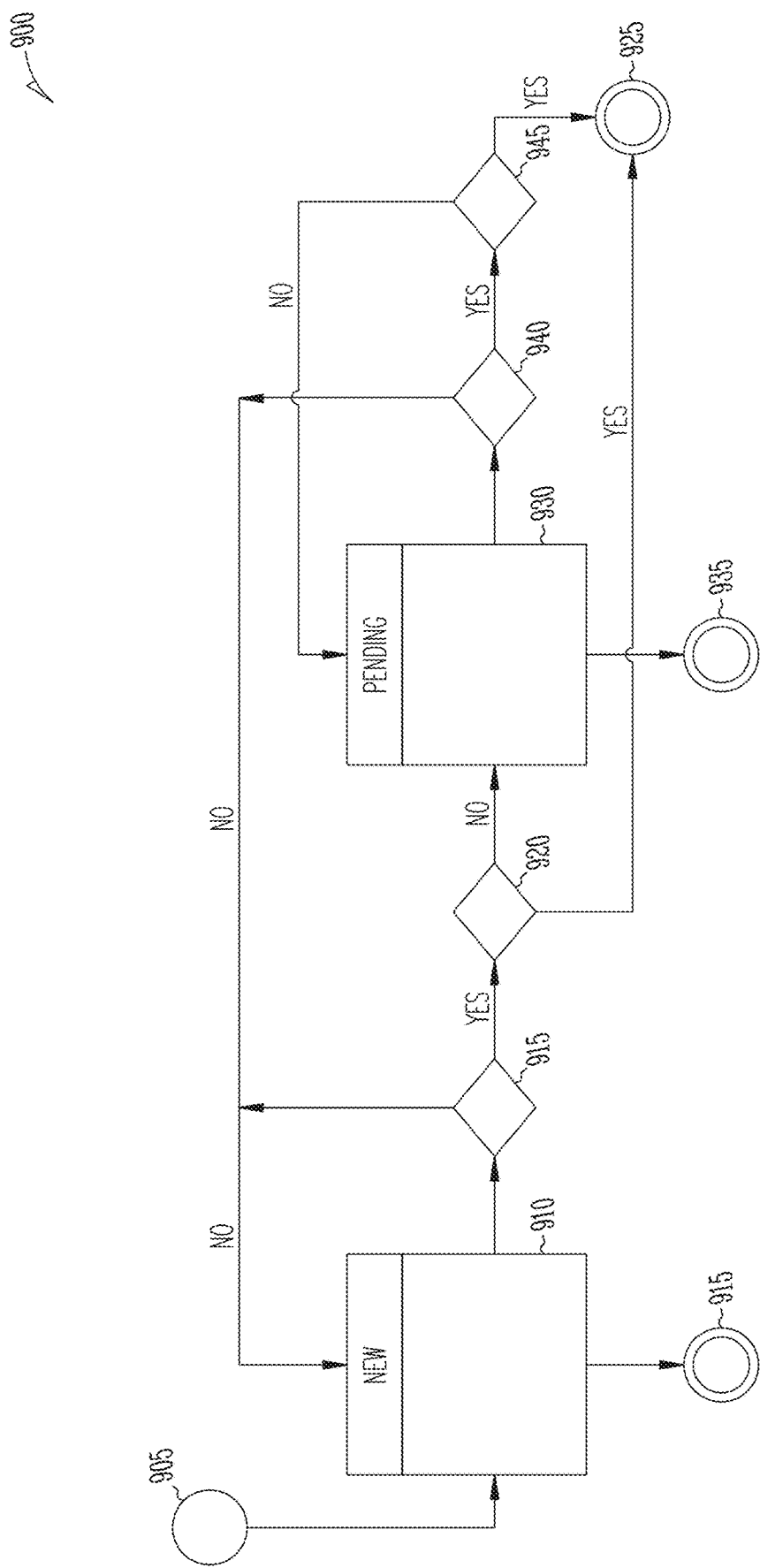
FIG. 9 illustrates a lifecycle of an opportunity in sample embodiments.

FIG. 9 illustrates a lifecycle 900 of an opportunity in sample embodiments. As illustrated, the opportunity system, such as a pharmacy analytics systems such as a data warehouse system provided by 1010Data, evaluates pharmacy data to identify opportunities at 905. The identified opportunity is forwarded to the pharmacy management system mainframe as a New opportunity 910. If not received in the next daily feed from the opportunity system, the New opportunity may become Deleted.

The New opportunity is evaluated at 915 to determine if at least one action is performed. If so, it is determined at 920 whether the user is a registered pharmacist. If no action is performed, the process returns to 910 to process a New opportunity. If the user is a registered pharmacist, the process is Closed at 925. If the user is determined at 920 to not be a registered pharmacist, the opportunity moves to a Pending state at 930. If not received in the next daily feed from the opportunity system, the Pending opportunity may become Removed at 935.

The Pending opportunity is evaluated at 940 to determine if at least one action is performed. If so, it is determined at 945 whether the user is a registered pharmacist. If no action is performed, the process returns to 930 to process a Pending opportunity. If the user is a registered pharmacist, the process is Closed at 925. Otherwise, the process returns to 910 to process a New opportunity when received.

It will be appreciated that the systems and method described herein provide automatic identification of opportunities that may be presented in the workflow of the pharmacist and presented at the point of sale.

System Configuration

Techniques described herein may be used with one or more of the computer systems described herein and/or with one or more other systems. For example, the various procedures described herein may be implemented with hardware or software, or a combination of both. For example, the processor, memory, storage, output device(s), input device(s), and/or communication connections discussed below can each be at least a portion of one or more hardware components. Dedicated hardware logic components can be constructed to implement at least a portion of one or more of the techniques described herein. For example, and without limitation, such hardware logic components may include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc. Applications that may include the apparatus and systems of various aspects can broadly include a variety of electronic and computer systems. Techniques may be implemented using two or more specific interconnected hardware modules or devices with related control and data signals that can be communicated between and through the modules, or as portions of an application-specific integrated circuit. Additionally, the techniques described herein may be implemented by software programs executable by a computer system. As an example, implementations can include distributed processing, component/object distributed processing, and parallel processing. Moreover, virtual computer system processing can be constructed to implement one or more of the techniques or functionality, as described herein.

Figure 10:
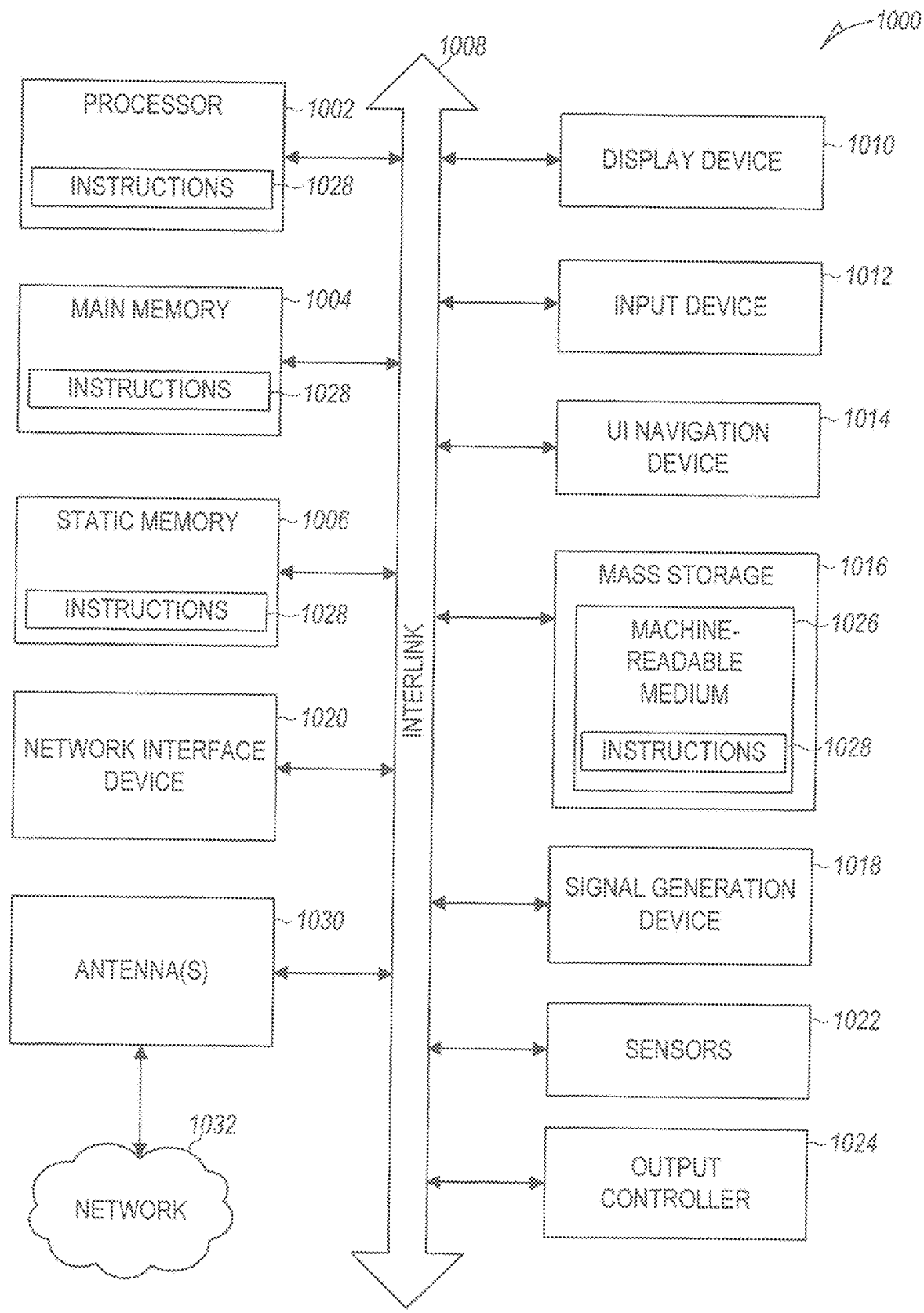
FIG. 10 illustrates a block diagram of an example of a machine upon which one or more embodiments may be implemented.

FIG. 10 illustrates a block diagram of an example of a machine 1000 upon which one or more embodiments may be implemented. In alternative embodiments, the machine 1000 may operate as a standalone device or may be connected (e.g., networked) to other machines. In a networked deployment, the machine 1000 may operate in the capacity of a server machine, a client machine, or both in server-client network environments. In an example, the machine 1000 may act as a peer machine in peer-to-peer (P2P) (or other distributed) network environment. In sample embodiments, the machine 1000 may be used in embodiments of the pharmacy management system mainframe as well as the user devices 130 and 132, point of sale system 114, and pharmacy system 112 and may be a personal computer (PC), a tablet PC, a set-top box (STB), a personal digital assistant (PDA), a mobile telephone, a smart phone, a web appliance, a server, a network router, switch or bridge, or any machine capable of executing instructions (sequential or otherwise) that specify actions to be taken by that machine. For example, machine 1000 may serve as a workstation, a front-end server, or a back-end server of a communication system. Machine 1000 may implement the methods described herein (e.g., FIGS. 2-7 and 9) by running software that includes instructions that, when processed, implement the methods described herein. Further, while only a single machine 1000 is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, processors, logic, or a number of components, modules, or mechanisms (herein "modules"). Modules are tangible entities (e.g., hardware) capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine readable medium. The software, when executed by the underlying hardware of the module, causes the hardware to perform the specified operations.

Accordingly, the term "module" is understood to encompass a tangible hardware and/or software entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software, the general-purpose hardware processor may be configured as respective different modules at different times. Software may accordingly configure a hardware processor, for example, to constitute a particular module at one instance of time and to constitute a different module at a different instance of time.

Machine (e.g., computer system) 1000 may include a hardware processor 1002 (e.g., a central processing unit (CPU), a graphics processing unit (GPU), a hardware processor core, or any combination thereof), a main memory 1004 and a static memory 1006, some or all of which may communicate with each other via an interlink (e.g., bus) 1008. The machine 1000 may further include a display unit 1010 (shown as a video display), an alphanumeric input device 1012 (e.g., a keyboard), and a user interface (UI) navigation device 1014 (e.g., a mouse or pen). In an example, the display unit 1010, input device 1012 and UI navigation device 1014 may be a touch screen display. In sample embodiments of the machine 1000, the input device 1012 may include a microphone and/or a video recorder. The machine 1000 may additionally include a mass storage device (e.g., drive unit) 1016, a signal generation device 1018 (e.g., a speaker), a network interface device 1020, and one or more sensors 1022. Example sensors 1022 include one or more of a global positioning system (GPS) sensor, compass, accelerometer, temperature, light, camera, video camera, sensors of physical states or positions, pressure sensors, fingerprint sensors, retina scanners, or other sensors. The machine 1000 may include an output controller 1024, such as a serial (e.g., universal serial bus (USB), parallel, or other wired or wireless (e.g., infrared(IR), near field communication (NFC), etc.) connection to communicate or control one or more peripheral devices (e.g., a printer, card reader, etc.).

The mass storage device 1016 may include a machine readable medium 1026 on which is stored one or more sets of data structures or instructions 1028 (e.g., software) embodying or utilized by any one or more of the techniques or functions described herein. The instructions 1028 may also reside, completely or at least partially, within the main memory 1004, within static memory 1006, or within the hardware processor 1002 during execution thereof by the machine 1000. In an example, one or any combination of the hardware processor 1002, the main memory 1004, the static memory 1006, or the mass storage device 1016 may constitute machine readable media.

While the machine readable medium 1026 is illustrated as a single medium, the term "machine readable medium" may include a single medium or multiple media (e.g., a centralized or distributed database, and/or associated caches and servers) configured to store the one or more instructions 1028. The term "machine readable medium" may include any medium that is capable of storing, encoding, or carrying instructions for execution by the machine 1000 and that cause the machine 1000 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; Random Access Memory (RAM); Solid State Drives (SSD); and CD-ROM and DVD-ROM disks. In some examples, machine readable media may include non-transitory machine-readable media. In some examples, machine readable media may include machine readable media that is not a transitory propagating signal.

The instructions 1028 may further be transmitted or received over communications network 1032 using a transmission medium via the network interface device 1020. The machine 1000 may communicate with one or more other machines utilizing any one of several transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®), IEEE 802.15.4 family of standards, a Long Term Evolution (LTE) family of standards, a Universal Mobile Telecommunications System (UMTS) family of standards, peer-to-peer (P2P) networks, among others. In an example, the network interface device 1020 may include one or more physical jacks (e.g., Ethernet, coaxial, or phone jacks) or one or more antennas to connect to the communications network 1032. In an example, the network interface device 1020 may include a plurality of antennas to wirelessly communicate using at least one of single-input multiple-output (SIMO), multiple-input multiple-output (MIMO), or multiple-input single-output (MISO) techniques. In some examples, the network interface device 1020 may wirelessly communicate using Multiple User MIMO techniques.

EXAMPLES

In addition to the clinical services system, the examples include:

Example 1 is a method of providing clinical services comprising: analyzing pharmacy data to generate clinical opportunities for patients; providing a file containing the clinical opportunities to a central pharmacy management system; the central pharmacy management system distributing clinical opportunities to pharmacy management systems in respective pharmacies based on customers registered with each respective pharmacy; and presenting clinical opportunities for a customer during interactions with the customer in a prescription workflow when filling prescriptions using a pharmacy management system.

Example 2 is a method as in Example 1 further comprising a Point of Sale (POS) system in the pharmacy at which the customer is registered presenting clinical opportunities for the customer when concluding a sale for a prescription.

Example 3 is a method as in any preceding example wherein the clinical opportunities include at least one of an immunization, medication therapy management, performance measurement, and predictive refill.

Example 4 is a method as in any preceding example further comprising providing a configuration portal that enables a user to add and to configure clinical opportunities and actions associated with the generated clinical opportunities.

Example 5 is a method as in any preceding example further comprising the configuration portal enabling the user to search for clinical programs including clinical opportunities based on a program description for the clinical programs and a designated user level.

Example 6 is a method as in any preceding example further comprising the configuration portal enabling the user to add a new clinical program and a user level.

Example 7 is a method as in any preceding example further comprising the configuration portal enabling the user to specify a suppression type for a clinical program, wherein a suppression type for a clinical program suppresses clinical opportunities for the customer during the prescription workflow.

Example 8 is a method as in any preceding example further comprising the configuration portal enabling the user to edit at least a program description, a user level, and the suppression type for a clinical program from a clinical program search screen.

Example 9 is a method as in any preceding example further comprising the configuration portal enabling the user to create a clinical opportunity and to assign and unassign actions to a clinical opportunity.

Example 10 is a method as in any preceding example further comprising the configuration portal enabling the user to assign and unassign web links to a clinical opportunity.

Example 11 is a method as in any preceding example further comprising the configuration portal enabling the user to add and to edit clinical opportunities.

Example 12 is a method as in any preceding example further comprising the configuration portal enabling the user to search for an action associated with one or more clinical programs.

Example 13 is a method as in any preceding example further comprising the central pharmacy management system processing the file containing the clinical opportunities in response to user queries to identify clinical opportunities at one or more pharmacies at which the customer is registered.

Example 14 is a method as in any preceding example further comprising the central pharmacy management system periodically synchronizing new data from the processed file, actions taken by the pharmacy management system when responding to a clinical opportunity, and configuration data among the central pharmacy management system and the pharmacy management system.

Example 15 is a method as in any preceding example further comprising synchronizing actions to be taken in response to respective clinical opportunities between the central pharmacy management system and the one or more pharmacies at which the customer is registered.

Example 16 is a method as in any preceding example further comprising de-identifying a clinical opportunity in a list of available clinical opportunities when a patient has indicated interest in the clinical opportunity, an action has been taken to address the clinical opportunity, and a pharmacist has reviewed the action taken.

Example 17 is a method as in any preceding example further comprising inserting a clinical opportunities screen into the prescription workflow when filling prescriptions using the pharmacy management system and providing a search interface that enables a user to search for available clinical opportunities and to launch a selected clinical opportunity to perform identified activities.

Example 18 is a method as in any preceding example further comprising inserting a clinical opportunities screen into a checkout process at the POS system that presents available opportunities for a patient during the checkout process.

Example 19 is a method as in any preceding example wherein presenting clinical opportunities for a customer during interactions with the customer in a prescription workflow when filling prescriptions using a pharmacy management system in a pharmacy at which the customer is registered comprises presenting a clinical opportunities screen to a display, the clinical opportunities screen being configurable on the display based on priorities of the clinical opportunities.

Example 20 is a method as in any preceding example further comprising adding a "Patient not interested" button to a clinical opportunity on the clinical opportunities screen when a patient has indicated no interest in the clinical opportunity.

Example 21 is a method as in any preceding example wherein presenting the clinical opportunities screen comprises presenting a button that, upon selection, allows a user to access a clinical opportunity search screen.

Example 22 is a method as in any preceding example further comprising launching a clinical opportunity from search results on the clinical opportunity search screen.

Example 23 is a method as in any preceding example further comprising automatically launching the clinical opportunities screen after a user has selected a medication using the pharmacy management system or when the user opens a prescription in a product review status.

Example 24 is a method as in any preceding example further comprising suppressing a clinical opportunity during the prescription workflow when a prescription being dispensed addresses the clinical opportunity.

Example 25 is a method as in any preceding example further comprising adding a dedicated button on a medication history screen of the pharmacy management system that launches a clinical opportunities screen for the patient upon selection.

Example 26 is a method as in any preceding example further comprising adding a dedicated button on an order summary screen of the pharmacy management system that launches a clinical opportunities screen for the patient upon selection.

Example 27 is a method as in any preceding example further comprising presenting available clinical opportunities to a user of the pharmacy management system when the pharmacy management system is in a product review status irrespective of whether or not the clinical opportunity already has been addressed.

Example 28 is a method as in any preceding example further comprising capturing a list of clinical opportunities shown to a user of the pharmacy management system in the prescription workflow and preparing a report including the list of clinical opportunities.

Example 29 is a method as in any preceding example further comprising suppressing a clinical opportunity at a second pharmacy where the customer is registered when the clinical opportunity has been acted upon in the pharmacy at which the customer is registered.

Example 30 is a method as in any preceding example further comprising removing clinical opportunities from the central pharmacy management system as the clinical opportunities reach their expiration dates and maintaining a record of actions taken with respect to clinical opportunities.

In the above Detailed Description, various features may be grouped together to streamline the disclosure. However, the claims may not set forth every feature disclosed herein as embodiments may feature a subset of the features. Further, embodiments may include fewer features than those disclosed in a particular example. Also, although the subject matter has been described in language specific to structural features and/or methodological acts, it is to be understood that the subject matter defined in the appended claims is not necessarily limited to the specific embodiments, features, or acts described above. Rather, the specific embodiments, features, and acts described above are disclosed as example forms of implementing the claims. Thus, the following claims are hereby incorporated into the Detailed Description, with a claim standing on its own as a separate embodiment.

What is claimed is:

1. A clinical services system comprising:
an opportunity system that analyzes pharmacy data to generate clinical opportunities for a customer and generates a file containing the clinical opportunities for the customer, wherein the clinical opportunities include clinical services for which the customer has met defined circumstances for the clinical services;
a central pharmacy management system that receives the file containing the clinical opportunities for the customer and distributes the clinical opportunities to pharmacy management systems in respective pharmacies where the customer has registered to receive at least one of a clinical service or a prescription; and
a pharmacy management system in a pharmacy at which the customer has registered, the pharmacy management system implementing a prescription workflow to fill prescriptions and presenting clinical opportunities for the customer during interactions with the customer in the prescription workflow.

2. The system as in claim 1, further comprising a Point of Sale (POS) system in the pharmacy at which the customer has registered, the POS system presenting clinical opportunities for the customer when concluding a sale for a prescription.

3. The system as in claim 2, wherein the POS system inserts a clinical opportunities screen into a checkout process that presents available opportunities for the customer during the checkout process.

4. The system as in claim 1, wherein the clinical opportunities include at least one of an immunization, medication therapy management, performance measurement, or predictive refill of a prescription.

5. The system as in claim 1, further comprising a configuration portal that enables a user to add and to configure clinical opportunities and actions associated with the generated clinical opportunities.

6. The system as in claim 5, wherein the configuration portal enables the user to search for clinical programs including clinical opportunities based on a program description for the clinical programs and a designated user level.

7. The system as in claim 6, wherein the configuration portal enables the user to add a new clinical program and a user level.

8. The system as in claim 6, wherein the configuration portal enables the user to specify a suppression type for a clinical program, wherein a suppression type for a clinical program suppresses clinical opportunities for the customer during the prescription workflow.

9. The system as in claim 8, wherein the configuration portal provides a clinical program search screen and enables the user to edit at least a program description, a user level, and the suppression type for a clinical program from the clinical program search screen.

10. The system as in claim 6, wherein the configuration portal enables the user to search for an action associated with one or more clinical programs.

11. The system as in claim 5, wherein the configuration portal enables the user to create a clinical opportunity and to assign and unassign actions to a clinical opportunity.

12. The system as in claim 5, wherein the configuration portal enables the user to assign and unassign web links to a clinical opportunity.

13. The system as in claim 5, wherein the configuration portal enables the user to add and to edit clinical opportunities.

14. The system as in claim 1, wherein the central pharmacy management system processes the file containing the clinical opportunities in response to user queries to identify clinical opportunities at one or more pharmacies at which the customer has registered.

15. The system as in claim 14, wherein the central pharmacy management system periodically synchronizes new data from the processed file, actions taken by the pharmacy management system when responding to a clinical opportunity, and configuration data among the central pharmacy management system and the pharmacy management system.

16. The system as in claim 15, wherein the central pharmacy management system synchronizes actions to be taken in response to respective clinical opportunities between the central pharmacy management system and the one or more pharmacies at which the customer has registered.

17. The system as in claim 16, wherein the pharmacy management system de-identifies a clinical opportunity in a list of available clinical opportunities when the customer has indicated interest in the clinical opportunity, an action has been taken to address the clinical opportunity, and a pharmacist has reviewed the action taken.

18. The system as in claim 1, wherein the pharmacy management system inserts a clinical opportunities screen into the prescription workflow when filling prescriptions and provides a search interface that enables a user to search for available clinical opportunities and to launch a selected clinical opportunity to perform identified activities.

19. The system as in claim 1, wherein the pharmacy management system presents a clinical opportunities screen to a display, the clinical opportunities screen being configurable on the display based on priorities of the clinical opportunities.

20. The system as in claim 19, wherein the pharmacy management system adds a "Patient not interested" button to a clinical opportunity on the clinical opportunities screen when the customer has indicated no interest in the clinical opportunity.

21. The system as in claim 19, wherein the clinical opportunities screen comprises a button that, upon selection, allows a user to access a clinical opportunity search screen.

22. The system as in claim 21, wherein the clinical opportunity search screen includes means for launching a clinical opportunity from search results on the clinical opportunity search screen.

23. The system as in claim 19, wherein the pharmacy management system automatically launches the clinical opportunities screen after a user has selected a medication or when the user opens a prescription in a product review status.

24. The system as in claim 1, wherein the pharmacy management system suppresses a clinical opportunity during the prescription workflow when a prescription being dispensed addresses the clinical opportunity.

25. The system as in claim 1, wherein the pharmacy management system comprises a dedicated button on a medication history screen that launches a clinical opportunities screen for the customer upon selection.

26. The system as in claim 1, wherein the pharmacy management system comprises a dedicated button on an order summary screen that launches a clinical opportunities screen for the customer upon selection.

27. The system as in claim 1, wherein the pharmacy management system presents available clinical opportunities to a user of the pharmacy management system when the pharmacy management system is in a product review status irrespective of whether or not the clinical opportunity already has been addressed.

28. The system as in claim 1, wherein the pharmacy management system comprises captures a list of clinical opportunities shown to a user of the pharmacy management system in the prescription workflow and prepares a report including the list of clinical opportunities.

29. The system as in claim 1, wherein the central pharmacy management system suppresses a clinical opportunity at a second pharmacy where the customer is registered when the clinical opportunity has been acted upon in the pharmacy at which the customer is registered.

30. The system as in claim 1, wherein the central pharmacy management system removes clinical opportunities as the clinical opportunities reach their expiration dates and maintains a record of actions taken with respect to clinical opportunities.

\* \* \* \* \*